(12) United States Patent
Dervan et al.

(10) Patent No.: US 7,713,701 B2
(45) Date of Patent: May 11, 2010

(54) DNA-BINDING POLYMERS

(75) Inventors: Peter B. Dervan, San Marino, CA (US);
Shane Foister, Philadelphia, PA (US);
Raymond Doss, Clark, NJ (US);
Michael A. Marques, San Mateo, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/238,167

(22) Filed: Sep. 25, 2008

(65) Prior Publication Data
US 2009/0155202 A1   Jun. 18, 2009

Related U.S. Application Data

(62) Division of application No. 11/038,506, filed on Jan. 18, 2005, now Pat. No. 7,452,730.

(60) Provisional application No. 60/536,919, filed on Jan. 16, 2004.

(51) Int. Cl.
*C12Q 1/68* (2006.01)
*G01N 33/53* (2006.01)
*G01N 33/566* (2006.01)
*C07H 21/02* (2006.01)

(52) U.S. Cl. .................. 435/6; 435/5; 435/7.1; 435/7.2; 536/23.1; 436/501

(58) Field of Classification Search ............... 435/5, 435/6, 7.1, 7.2; 536/23.1; 436/501
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,133,974 A | 7/1992 | Paradissis et al. |
| 5,407,686 A | 4/1995 | Patel et al. |
| 5,624,898 A | 4/1997 | Frey, II |
| 5,736,152 A | 4/1998 | Dunn |
| 6,180,603 B1 | 1/2001 | Frey, II |

OTHER PUBLICATIONS

Arcamone, et al., "Structure and Synthesis of Distamycin A" *Nature* 203:1064-1065 (1964).
Baird and Dervan, "Solid Phase Synthesis of Polyamides Containing Imidazole and Pyrrole Amino Acids" *J. Am. Chem. Soc.* 118:6141-6146 (1996).
Behrens, et al., "Synthesis of a Hoechst 32258 Analogue Amino Acid Building Block for Direct Incorporation of a Fluorescent, High-Affinity DNA Binding Motif into Peptides" *Bioconjugate Chem.* 12:1021-1027 (2001).

(Continued)

*Primary Examiner*—Jezia Riley
(74) *Attorney, Agent, or Firm*—Foley & Lardner LLP

(57) ABSTRACT

Methods and compositions are provided for forming complexes between dsDNA and novel DNA-binding polymers comprising N-terminal thiophene-containing moieties which exhibit selectivity for T-A base pairs. By appropriate choice of target sequences and DNA-binding polymers, complexes comprising polymer-DNA are obtained with high association constants. The formation of complexes can be used for identification of specific dsDNA sequences, for inhibiting gene transcription, and as a therapeutic for inhibiting proliferation of undesired cells or modulation of expression of specific genes.

21 Claims, 6 Drawing Sheets

OTHER PUBLICATIONS

Briehn, et al., "Alternative Heterocycles for DNA Recognition: The Benzimidazole/Imidazole Pair" *Chem. Eur. J.* 9:2110-2122 (2003).

Church, et al., "N-(2-Chloroethyl)-N-Nitrosoureas Covalently Bound to Nonionic and Monocationic Lexitropsin Dipeptides. Synthesis, DNA Affinity Binding Characteristics, and Reactions with $^{32}$P-End-Labeled DNA" *Biochemistry* 29:6827-6838 (1990).

Clanton, et al., "Novel Sulfonated and Phosphonated Analogs of Distamycin Which Inhibit he Replication of HIV" *Antiviral Res.* 27:335-354 (1995).

Dervan, et al., "Sequence-Specific DNA Recognition by Polyamides" *Current Opinion in Chemical Biology*, 3:688-693 (1999).

Ellervik et al., "Hydroxybenzamide/Pyrrole Pair Distinguishes T•A from A•T Base Pairs in the Minor Groove of DNA" 122:9354-9360 (2000).

Gottesfeld, et al., "Regulation of Gene Expression by Small Molecules" *Nature* 387:202-205 (1997).

Graham, et al., "Manipulation of Adenovirus Vectors" *Methods in Molecular Biology* 7:109-128 (1991).

He, et al., "Microgonotropens and Their Interactions with DNA. 1. Synthesis of the Tripyrrole Peptides Dien-Microgonotropen-a, -b, and -c and Characterization of Their Interactions with dsDNA" *J. Am. Chem. Soc.* 115:7061-7071 (1993).

Ji, et al., "Tris-Benzimidazole Derivatives: Design, Synthesis and DNA Sequence Recognition" *Bioorg. Med. Chem.* 9:2905-2919 (2001).

Kielkopf, et al., "Structural Basis for G•C Recognition in the DNA Minor Groove" *Nature Struct. Biol.* 5:104-109 (1998).

Kielkopf et al., "A Structural Basis for Recognition of A•T and T•A Base Pairs in the Minor Groove of B-DNA" *Science* 282:111-115 (1998).

Kumar, et al., "Sequence Specific Molecular Recognition and Binding by a GC Recognizing Hoechst 33258 Analogue to the Decadeoxynbonucleotide d-[CATGGCCATG]: Structural and Dynamic Aspects Deduced from High Field $^1$H-NMR Studies" *J. Biomol. Struct. Dyn.* 8:331-357 (1990).

Lewin, B., "Promoters for RNA Polymerase II Have Short Sequence Elements" *Genes* 831-835 (1997).

Lombardy, et al., "Synthesis and DNA Interactions of Benzimidazole Dications Which Have Activity Against Opportunistic Infections" *J. Med. Chem.* 39:1452-1462 (1996).

Marques, et al., "Toward an Understanding of the Chemical Etiology for DNA Minor-Groove Recognition by Polyamides" *Helvetica Chimica Acta* 85:4485-4517 (2002).

Matsuba, et al., "A Novel Synthetic DNA Minor Groove Binder, MS-247: Antitumor Activity and Cytotoxic Mechanism" *Cancer Chemother, Pharmacol.* 46:1-9 (2000).

Minehan, et al., "Molecular Recognition of DNA by Hoechst Benzimidazoles: Exploring Beyond the Pyrrole-Imidazole-Hydroxypyrrole Polyamide-Pairing Code" *Helvetica Chimica Acta* 83:2197-2213 (2000).

Pelton and Wemmer, "Structural Characterization of a 2:1 Distamycin A•d(CGCAAATTGGC) Complex by Two-Dimensional NMR" *Proc Natl Acad Sci USA* 86:5723-5727 (1989).

Pjura, et al., "Binding of Hoechst 33258 to the Minor Groove of B-DNA" *J. Mol. Biol.* 197:257-271 (1987).

Renneberg and Dervan, "Imidazopyridine/Pyrrole and Hydroxybenzimidazole/Pyrrole Pairs for DNA Minor Groove Recognition" *JACS* 125:5707-5716 (2003).

Satz and Bruice, "Recognition of Nine Base Pairs in the Minor Groove of DNA by a Tripyrrole Peptide-Hoechst Conjugate" *J. Am. Chem. Soc.* 123:2469-2477 (2001)

Taylor and Zhou, "A Facile Synthesis of 3-Fluorothiophene-2-Carboxylic Acid" 29:221-223 (1997).

Teng, et al., "The Molecular Structure of the Complex of Hoechst 33258 and the DNA Dodecamer d(CGCGAATTCGCG)" *Nucleic Acids Res.* 16:2671-2690 (1988).

Trauger, and Dervan, "Footprinting Methods for Analysis of Pyrrole-Imidazole Polyamide/DNA Complexes" *Methods Enzymol.* 340:450-466 (2001).

Wang, et al., "Evaluation of the Influence of Compound Structure on Stacked-Dimer Formation in the DNA Minor Groove" *Biochemistry* 40:2511-2521 (2001).

White, et al., "On the Pairing Rules for Recognition in the Minor Groove of DNA by Pyrrole-Imidazole Polyamides" *Chemistry & Biology* 4:569-578 (1997).

White et al., "Recognition of the Four Watson-Crick Base Pairs in the DNA Minor Groove by Synthetic Ligands" *Nature* 391:468-471 (1998).

Yamamoto, et al., "Synthesis and DNA Binding Properties of Amide Bond-Modified Analogues Related to Distamycin" *Tetrahedron Letters* 37:7801-7804 (1996).

Zhang, et al., "A Novel Dicationic Polyamide Ligand Binds in the DNA Minor Groove as a Dimer" *FEBS Lett.* 509:85-89, (2001).

(a)

(b)

(c)

SEQUENCE LISTING

<160> NUMBER OF SEQ ID NOS: 4

<210> SEQ ID NO 1
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aattcgagct cggtaccggg g                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggcacgac aggtttcccg a                                          21

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: a or t

<400> SEQUENCE: 3 catntacata                                                       10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: complimentary nucleotide to the variable in
      SEQ ID NO: 3, a or t

<400> SEQUENCE: 4 tatgtanatg                                                       10
```

DNA-BINDING POLYMERS

CROSS-REFERENCE TO RELATED PATENT APPLICATIONS

This application is a Divisional Application of U.S. Nonprovisional application Ser. No. 11/038,506, filed Jan. 18, 2005 which is a Continuation in Part of U.S. Provisional Application 60/536,919, filed Jan. 16, 2004, the entire contents of which are incorporated herein by reference. This application also incorporates by reference the entire contents of U.S. Nonprovisional application Ser. No. 10/794,584 filed Mar. 4, 2004.

STATEMENT OF GOVERNMENT SUPPORT

The U.S. Government has certain rights in this invention pursuant to Grant No. GM 27681 awarded by the National Institutes of Health.

FIELD OF THE INVENTION

The present invention relates to DNA-binding polymers comprising an N-terminal thiophene-containing moiety, wherein such polymers are capable of binding to predetermined sequences of double stranded DNA, containing a T-A base pair in the 5'-position. This invention is also related to detection of specific DNA sequences and modulation of transcription of target genes.

BACKGROUND OF THE INVENTION

The information provided herein and references cited are provided solely to assist the understanding of the reader, and does not constitute an admission that any of the references or information are prior art to the present invention.

With the explosion of techniques for the synthesis, analysis and manipulation of nucleic acids, numerous new opportunities have arisen in diagnostics and therapeutics. In research there is substantial interest in being able to identify DNA sequences, which may be associated with specific organisms, alleles, mutations, and the like, to understand particular genetic processes, to identify diseases, for forensic medicine, etc. Also, for many purposes, one may wish to modulate the expression of a target gene, so as to identify the function of such gene, or the cellular changes brought about by changes in the expression of such gene. In therapeutics, one may wish to inhibit the proliferation of cells, such as bacterial, fungal and chlamydia cells, which may act as pathogens, of viruses, of mammalian cells, where proliferation results in adverse effects on the host, or other situations. In vivo, one may provide for reversible or irreversible knock out, so that information can be generated on fetal development, or the effect on the organism of reduced levels of one or more genetic products.

Polyamide oligomers of nitrogen-containing five-membered heterocycles can be used to bind predetermined sequences of double stranded DNA (dsDNA). DNA recognition by polyamide oligomers depends on specific acid pairings that are oriented in the amino to carboxyl direction with respect to the 5'-3' direction of the DNA helix. Thus, polyamide oligomers bind dsDNA in an antiparallel fashion and in a stoichiometric ratio of 1:1 or 1:2, oligomer to DNA (Dervan et al., Current Opinion in Chemical Biology, Vol. 3: 688, 1999). Antiparallel pairs of certain five-membered heterocycles preferentially bind to specific base pairs on duplex DNA. These antiparallel pairs have proven useful for the recognition of hundreds of predetermined DNA sequences by polyamide oligomers. Listed below in Table 1 are representative polyamide pairs of five-membered heterocycles and the DNA pairs that they preferentially bind to, referred to herein as the "pairing rules."

TABLE 1

Pairing Rules for Five-Membered Heterocyles

| Polyamide Pair* | DNA base pair recognition |
| --- | --- |
| Im/Py | G•C |
| Py/Im | C•G |
| Hp/Py | T•A |
| Py/Hp | A•T |

*Im = N-methyl imidazole; Py = N-methyl pyrrole; Hp = 3-hydroxypyrrole

The fidelity of minor groove recognition by N-terminal Im/Py pairings in hairpin polyamides can be rationalized by a combination of both stabilizing and destabilizing forces which favors the rotamer with N3 in the groove and N-methyl out. Rotation of a terminal Im residue in the opposite conformer, orienting N3 away from the minor groove, would create unfavorable lone pair interactions with the proximal carboxamide oxygen, disrupt a favorable hydrogen bond with the exocyclic amine of G, and project an N-methyl group to the DNA floor which is presumably sterically unfavorable. Specifically, Im/Py distinguishes G-C from C-G and both of these from T-A/A-T base pairs while a Py/Py pair binds both T-A and A-T in preference to G-C/C-G. The exocyclic amino group of guanine imparts G-C specificity to Im/Py pairs through formation of a specific hydrogen bond with N3 of Im. Binding of Py/Py is disfavored at G-C base pairs by destabilizing steric interactions between the C3-H of Py and the guanine amino group (White et al., Chem. Biol. 1997, 4, 569; Kielkopf et al., Nat. Struct. Biol. 1998, 5, 104). The replacement of C3-H of one Py with hydroxyl creates the Hp/Py pair which exploits the steric fit and hydrogen bond acceptor potential of thymine-O2 as well as the destabilizing step c interaction with the bulkier adenine ring to gain specificity for T-A (White et al., Nature 391, 468, 1998; Kielkopf et al., Science 282, 111, 1998).

The five-membered heterocycles described thus far in DNA-binding polyamide oligomers are analogues of the pyrrole ring. Their chemical design mimics the natural products netropsin and distamycin A, molecules which bind the minor groove of DNA (Arcamone, F. et al., Nature 203: 1064, 1964; Pelton, J. G. et al., Proc Natl Acad Sci USA 86: 5723-5727, 1989).

The above pairing rules have been used to design hundreds of synthetic ligands that bind predetermined DNA sequences. However, many sequences remain difficult to target, likely due to sequence dependent microstructure variations in minor groove width or curvature. Furthermore, the specificity of cofacial aromatic amino acid pairings depend on their context (position) within a given hairpin polyamide. For example, Im/Py pairings show comparable specificity for G-C at both terminal and internal positions. Conversely, Hp/Py pairings do not specify T-A at the N-terminus of hairpin polyamides (Ellervik et al., J. Am. Chem. Soc. 2000, 122, 9354). The context dependence of Hp is presumably a result of the conformational freedom inherent to an N-terminal aromatic residue. The absence of a second 'groove-anchoring' carboxamide allows terminal rings to bind DNA in either of two conformations. For a terminal Hp residue, a rotamer with the hydroxyl recognition element oriented away from the floor of the minor groove could be stabilized by intramolecular hydrogen bonding between the C3-OH and the carbonyl oxygen of the 2-carboxamide. For terminal 2-hydroxybenzamide residues, some measure of T-A selectivity was recovered by creating steric bulk at the 6-position to force the hydroxyl recognition element into the groove (Ellervik et al., J. Am. Chem. Soc. 2000, 122, 9354). However, N-terminal pairings capable of binding T-A, with affinity and specificity comparable to those of Im/Py for G-C, are desired.

Efforts have been devoted to extend the ensemble of five-membered heterocycles that are capable of cooperatively pairing with each other to recognize specific DNA base pairs. These efforts have, in part, been motivated by the instability of the Hp heterocycle towards acids and free radicals. Polyamide oligomers containing Hp are susceptible to such degradation, and a robust replacement for use in biological applications is desired.

A search for new five-membered heterocycles and new five-membered heterocycle pairs for sequence determination was recently attempted with little success (Marques, M. et al., *Helvetica Chimica Acta* 85: 4485-4517, 2002). Using molecular modeling from an X-ray crystallography structure of a polyamide oligomer bound to duplex DNA, analogs of the existing five-membered heterocycles were designed to optimize binding to the curvature and twist of minor-groove DNA. Analogs of Py (1-methyl-1H-pyrazole (Pz) and 1H-pyrrole (Nh)), Im (5-methylthiazole (Nt) and furan (Fr)), and Hip (3-hydroxythiopene (Ht)) were synthesized and investigated in polyamide pairs. Additional sulfur containing pyrrole analogs (4-methylthiazole (Th), 3-methylthiophene (Tn), and thiophene (Tp)) were also studied. The chemical structures of these analogs are shown below:

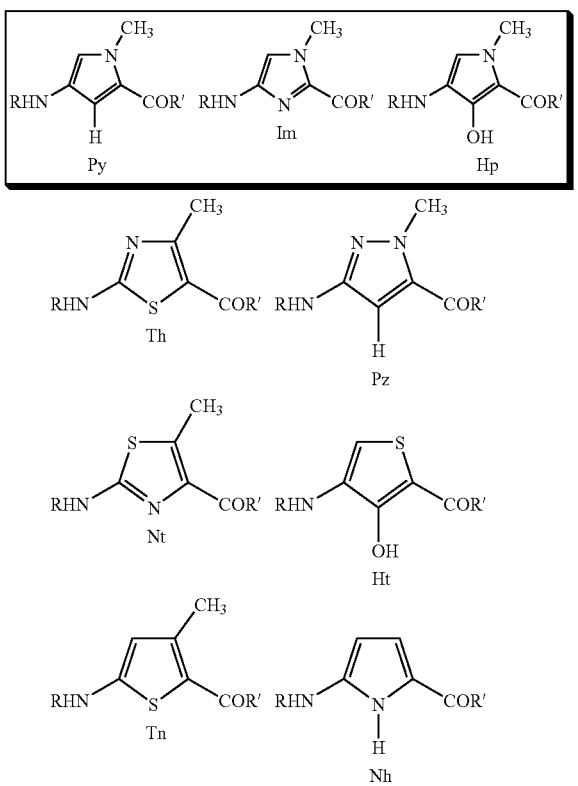

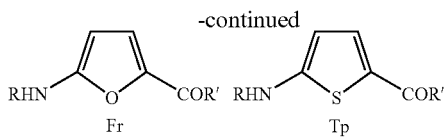

Six-membered heterocycles represent a new class of heterocycles that may be employed in compounds which bind DNA. Certain small molecule ligands known to bind the minor groove of DNA with relatively high affinities contain six-membered heterocycles and fused heterocycles, such as benzimidazole, imidazopyridines, and indoles (R. L. Lombardy, et al., *J. Med. Chem.*, 39: 1452-1462, 1996; Minehan, T. G. et al. *Helv. Chim. Acta*, 83: 2197-2213, 2000; Wang, L. et al., *Biochemistry*, 40: 2511-2521, 2001; Zhang, W. et al., *FEBS Lett.*, 509: 85-89, 2001; Ji, Y.-H. et al., *Bioorg. Med, Chem.*, 9: 2905-2919, 2001; Satz, A. L. et al., *J. Am. Chem. Soc.*, 123: 2469-2477, 2001; Behrens, C. et al., *Bioconjugate Chem*, 12: 1021-1027, 2001; Matsuba, Y. et al., *Cancer Chemother. Pharmacol.*, Vol. 46: 1-9, 2000).

Hoechst 33258, which comprises a bis-benzimidazole, an N-methylpiperazine, and a phenol moiety, is an example of a fused six-membered cyclic derivative (P. E. Pjura, K. Grzeskowiak, R. E. Dickerson, *J. Mol. Biol*, 197: 257-271, 1987; M. Teng, N. Usman, C. A. Frederick, A. Wang, *Nucleic Acids Res.*, 16: 2671-2690, 1988; S. Kumar, B. Yadagiri, J Zimmermann, R. T. Pon, J. W. Lown, *J. Biomol. Struct. Dyn.*, 8: 331-357, 1990). The chemical structure of Hoechst 33258 is shown below:

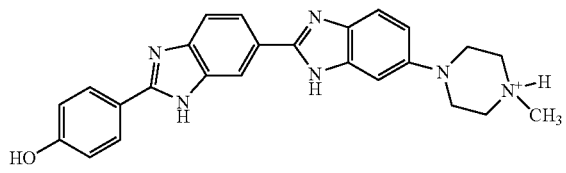

Hoechst 33258 is a highly fluorescent dye which binds the minor groove of DNA at A·T rich tracks. Oligomers of the Hoechst benzimidazoles have been synthesized and studied for DNA recognition (Minchan, T. G. et al., *Helvetica Chimica Acta* 83: 2197-2213, 2000). These benzimidazole oligomers also show preference for A·T rich sequences, as well as for 5'-WGWWW-3' and 5'-WCWWW-3', where W=A or T.

While Hoechst 33258 and its corresponding benzimidazole oligomers bind A·T rich DNA in a 1:1 ratio, such compounds do not recognize specific nucleotide base pairs across the duplex, such as in the pairing rules described above for five-membered heterocyclic polyamide oligomers. Other six-membered heterocyclic DNA binding ligands reported thus far also do not recognize specific mononucleotide base pairs across the duplex.

Thus, a need in the art for a T recognition element using the asymmetric cleft of a T-A base pair as the basis for shape selective discrimination has been identified.

SUMMARY OF THE INVENTION

In accordance with the present invention, there are provided novel DNA-binding polymers comprising optionally substituted oligomeric backbones and termini which bind specific base pairs on dsDNA in a 1:2 ratio of DNA-binding polymer to DNA oligonucleotide. These polymers represent a novel class of DNA binding ligands which are capable of binding to predetermined target sequence on dsDNA.

DNA-binding polymers presented herein are capable of forming a specific complex at targeted sequences within dsDNA. Polymeric compounds presented herein may also be used to detect the presence of a specific nucleotide sequence in dsDNA. Additionally, polymeric compounds herein can be used to isolate target dsDNA from a sample comprising a mixture of dsDNA. Furthermore, polymeric compounds herein are applicable in modulating transcription of a target gene in a cell. Effective amounts of polymeric compounds herein may be administered to a subject as a means of treating cancer by reducing the level of transcription of a target oncogene.

DETAILED DESCRIPTION OF THE INVENTION

Figure 1A:
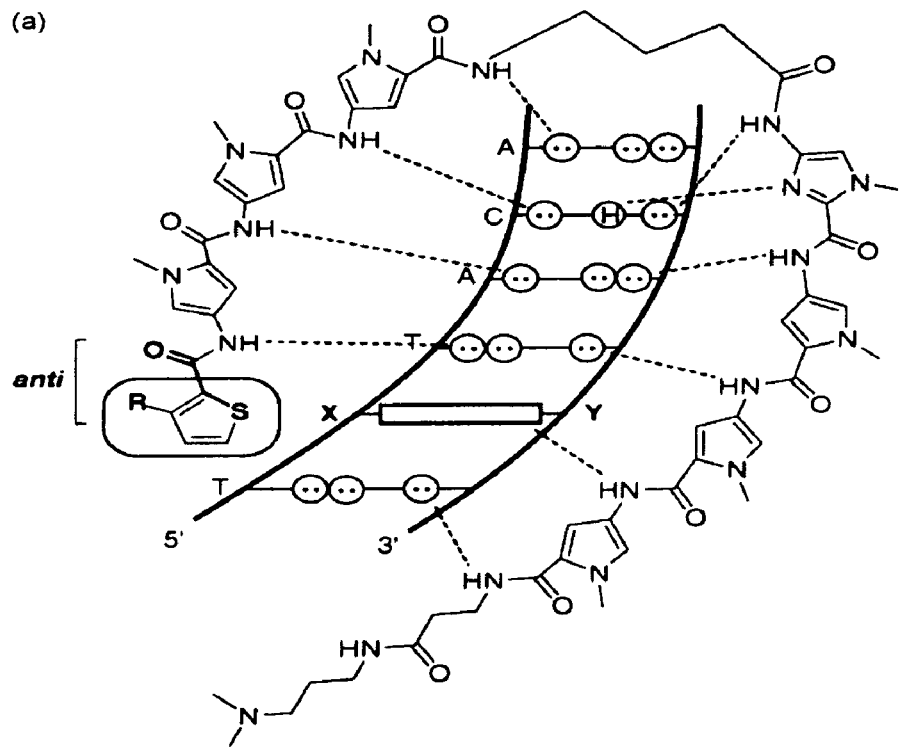
FIG. 1A-1B. Proposed binding models for DNA-binding polymers with 5'-TXTACA-3' site. A circle enclosing two dots represents lone pairs of N3 of purines and O2 of pyrimidines. A circle containing an H represents the exocyclic amine of guanine. Putative hydrogen bonds are indicated by dashed lines: (A) N-terminal residue drawn in "sulfur down" syn conformation; (B) N-terminal residue drawn in "sulfur up" anti conformation.
Figure 1B:
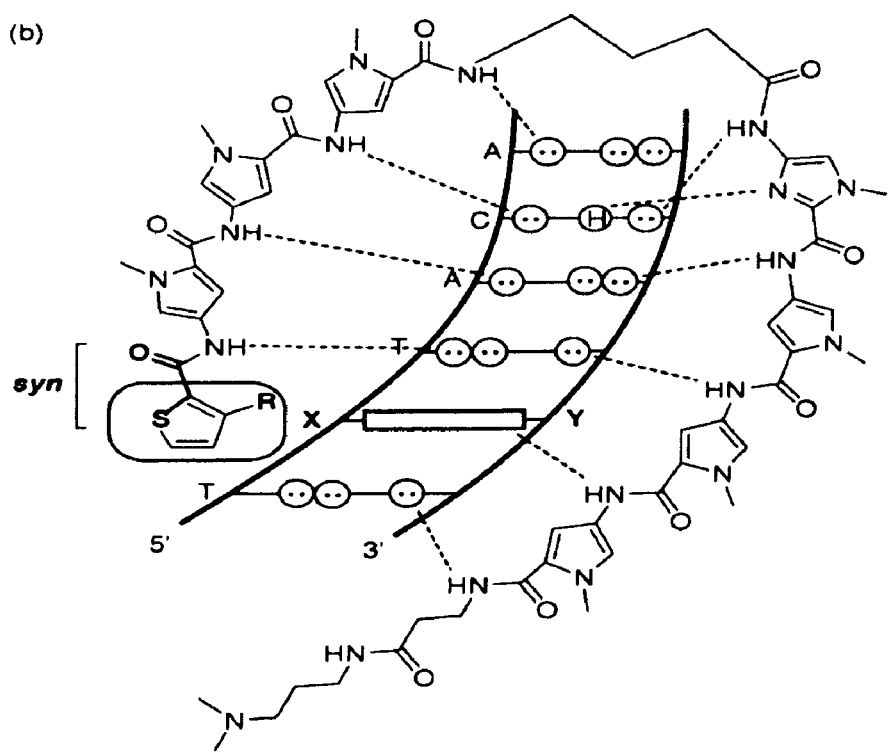
Figure 2:
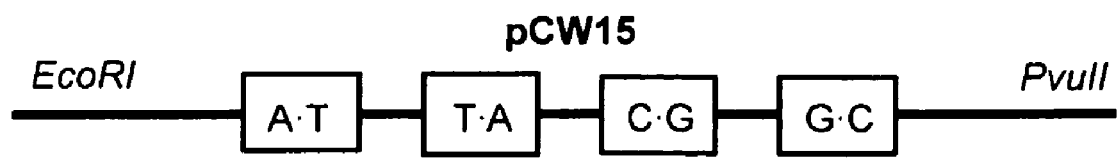
FIG. 2. (top) pCW15 plasmid design; (bottom) ball and stick model of hairpin polyamides varying the N-terminal residue. Shaded and non-shaded circles represent imidazole and pyrrole residues, respectively. A circle containing an S denotes an N-terminal thiophene (R=1-8) residue.
Figure 2:
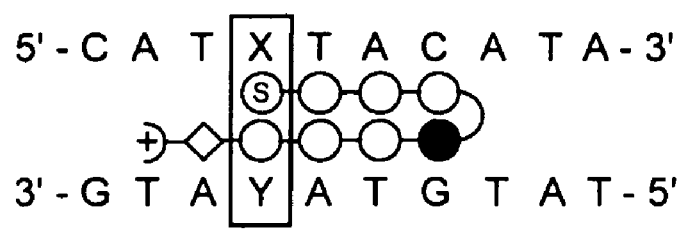
Figure 2:
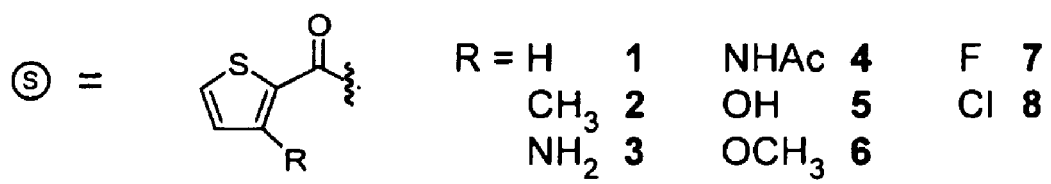
Figure 2:
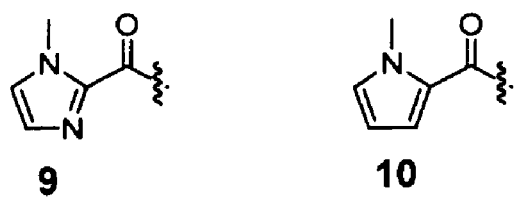

In one aspect, the present invention provides novel DNA-binding polymers comprising
a first terminus,
an oligomeric backbone optionally containing a linking element, and
a second terminus.

The DNA-binding polymer is effective to bind to a double-stranded DNA sequence having a number of DNA base pairs in the range (n/2) to (2n) where n is the number of monomer elements in the DNA-binding polymer.

In another aspect, the present invention provides a first terminus comprising optionally substituted thiophene-containing moieties. Exemplary thiophene-containing moieties include thiophene, benzthiophene, C—C linked benzimidazole/thiophene-containing moiety and C—C linked hydroxybenzimidazole/thiophene-containing moiety, and the like.

In still another aspect, the present invention provides a second terminus selected from the group consisting of optionally substituted N-methylpyrrole, optionally substituted N-methylimidazole, and optionally substituted benzimidazole moiety.

In yet another aspect, the present invention provides oligomeric backbones having the formula:

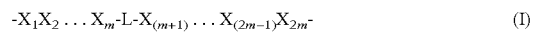

$$-X_1X_2\ldots X_m\text{-L-}X_{(m+1)}\ldots X_{(2m-1)}X_{2m}- \quad (I)$$

wherein:
each $X_1, X_2, X_m, X_{(m+1)}, X_{(2m-1)}$, and $X_{2m}$ is independently a monomer element in the binding pairs $X_1/X_{2m}$, $X_2/X_{(2m-1)}, \ldots, X_m/X_{(m+1)}$;
L is an optional linking element, and
m falls in the range of 1 up to 10.

Monomer elements contemplated for use in the practice of the present invention include optionally substituted pyrrole carboxamide monomer, optionally substituted imidazole carboxamide monomer, optionally substituted C—C linked heteromonocyclic/heterobicyclic moiety, and β-alanine. In the context of the present invention, the optionally substituted pyrrole carboxamide monomers have the structure:

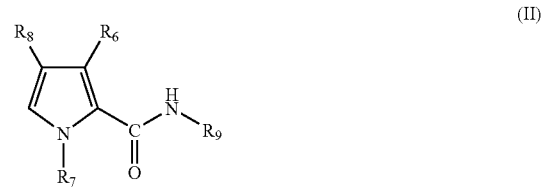

wherein:
$R_6$ is selected from the group consisting of H, CH$_3$, Cl, CF$_3$, OH and NH$_2$;
$R_7$ is selected from the group consisting of H, C$_{1-10}$ alkyl, C$_{2-10}$ alkenyl, and C$_{2-10}$ alkynyl;
$R_8$ is selected from the group consisting of hydrogen and a covalent bond; and
$R_9$ is a covalent bond.

Further in the context of monomer elements of the present invention, optionally substituted imidazole carboxamide monomers have the structure:

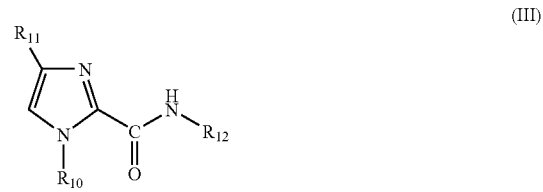

wherein:
R$_{10}$ is selected from the group consisting of C$_{1-10}$ alkyl, C$_{2-10}$ alkenyl, and C$_{2-10}$ alkynyl;
R$_{11}$ is selected from the group consisting of hydrogen and a covalent bond; and
R$_{12}$ is a covalent bond.

Further in the context of the present invention, optionally substituted C—C linked heteromonocyclic/heterobicyclic moieties have the structure

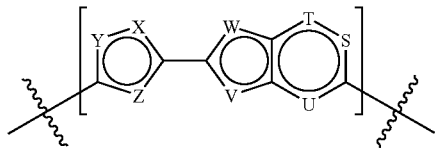

(IV)

wherein:
each of S, T, and U is independently —CR$_{13}$ or N;
each of V, W, X, Y and Z is independently —CR$_{14}$, N, —NR$_{15}$, O, or S; and
each R$_{13}$ is independently H, halogen, —OH, —OMe, —OAc, —NH$_2$, —NHAc, —CH$_3$, —SH, —NO$_2$, —CHO, —SO$_2$H, —S(O)NH$_2$, —(C≡C)(CN)$_3$, —CN, acetyl, C$_{1-6}$ alkyl, or C$_{1-6}$ alkylamino; and
each of R$_{14}$ and R$_{15}$ is independently H, halogen, —OH, —OMe, —SH, —CN, —OAc, —NH$_2$, —NHAc, C$_{1-6}$ alkyl, C$_{1-6}$ alkylamino, C$_{2-6}$ alkenyl, or C$_{2-6}$ alkynyl.

The present invention provides compounds of Formula (V):

(V)

or a pharmaceutically acceptable salt thereof, wherein:

T$_1$ is a first terminus comprising optionally substituted thiophene-containing moiety selected from the group consisting of thiophene, benzthiophene, C—C linked benzimidazole/thiophene-containing moiety and C—C linked hydroxybenzimidazole/thiophene-containing moiety;

each bond B is independently

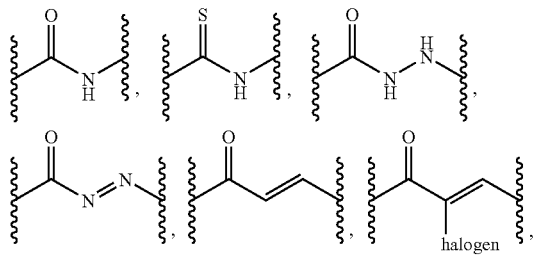

or a direct bond;

each monomer element M is independently

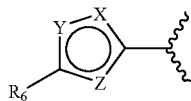

wherein:
each R$_6$, is independently H, halogen, NO, N-acetyl, CHO, benzyl, C$_1$-C$_{12}$ alkyl C$_2$-C$_{12}$ alkenyl, C$_2$-C$_{12}$ alkynyl, C$_1$-C$_{12}$ alkylamino, C$_1$-C$_{12}$ alkyldiamino, C$_1$-C$_{12}$ alkylamido, C$_1$-C$_{12}$ alkyldiamido, C$_1$-C$_{12}$ aminoalkylamido, C$_1$-C$_{12}$ aminoalkyldiamido, or C$_1$-C$_{12}$ alkylcarboxylate, with the proviso that when either p>1 or q>1, R$_6$ is a covalent bond,
optionally substituted C—C linked heteromonocyclic/heterobicyclic moiety, or
β-alanine;

each [B-M] pair appears p times where p is an integer in the range 1 to 10;

L is selected from the group consisting of optionally substituted C$_2$-C$_6$ alkyleneamino, optionally substituted C$_2$-C$_6$ alkylenediamino, optionally substituted C$_2$-C$_6$ alkyleneamido, optionally substituted C$_2$-C$_6$ alkylenecarboxylene, optionally substituted C$_2$-C$_6$ alkylene, optionally substituted C$_2$-C$_6$ alkenylene, optionally substituted C$_2$-C$_6$ alkynylene and optionally substituted polyethylene glycol diyl;

each [M-B] pair appears q times where q is an integer in the range 1 to 10;

T$_2$ is a second terminus selected from the group consisting of optionally substituted N-methylpyrrole, optionally substituted N-methylimidazole, and optionally substituted benzimidazole moiety; and $2 \leq p+q \leq 20$.

Accordingly, each [B-M] and [M-B] pair of Structure (V) is correlated with a corresponding monomer element "X" of Structure (I) wherein the designator "X" incorporates the monomer element linkage explicitly denoted by designator "B" in Structure (V). Thus, termini T$_1$ and T$_2$ as a pair correlate with the binding pair X$_1$/X$_{2m}$ of Structure (I).

As used herein, reference to a certain element such as hydrogen or H is meant to include all isotopes of that element. For instance, if a group is defined to include hydrogen or H, it also can include deuterium and/or tritium.

Compounds of the present invention may have asymmetric centers and may occur, except when specifically noted, as mixtures of stereoisomers or as individual diastereomers, or enantiomers, with all isomeric forms being included in the present invention. Compounds of the present invention embrace all conformational isomers, including, for example, cis- or trans-conformations. Compounds of the present invention may also exist in one or more tautomeric forms, including both single tautomers and mixtures of tautomers.

Moieties of the present invention may be substituted with various atoms as noted. The phrase "substitution" refers to an atom or group of atoms that has been replaced with another substituent. The phrase "substituted" includes all levels of substitution, e.g. mono-, di-, tri, tetra-, or penta-substitution, where such substitution is chemically permissible. Substitutions can occur at any chemically accessible position and on any atom, such as substitution(s) on carbon and any heteroatom, preferably oxygen, nitrogen, or sulfur. For example, substituted moieties are those where one or more bonds to a hydrogen or carbon atom(s) contained therein are replaced by a bond to non-hydrogen and/or non-carbon atom(s). Substitutions can include, but are not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

The phrase "substituted" or "substitution" also includes substitution with an optionally substituted hydrocarbyl moiety containing one or more of the following: —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—.

The phrase "oligomeric backbone" refers to a molecular fragment comprising a plurality of monomer elements connected to each other. Monomer elements within an oligomeric backbone may be the same or different from each other. The number of repeating monomer elements can vary depending on the particular application for which the oligomeric backbone is employed. Oligomeric backbones of the invention can comprise from 2 to 20 monomer elements, or such as from 4 to 15 monomeric elements, or such as from 8 to 12 monomeric elements. The connectivity between monomer elements can be the same or different throughout the oligomeric backbone.

The phrase "monomer element" refers to a bifunctional monomeric moiety containing an optionally substituted heterocycle, for example substituted pyrrole, optionally substituted imidazole, optionally substituted C—C linked heteromonocyclic/heterobicyclic moiety, or β-alanine.

The phrase "halogen" or "halide" refers to —F, —Cl, —Br. or —I.

The phrase "alkyl" refers to straight, branched chain, or cyclic hydrocarbyl groups comprising from 1 to 20 carbon atoms. The phrase "alkyl" includes straight chain alkyl groups such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and —CH(CH$_2$CH$_3$)CH(CH$_3$)CH(CH$_3$)(CH$_2$CH$_3$). Thus, alkyl groups includes primary alkyl groups, secondary alkyl groups, and tertiary alkyl groups. Preferred alkyl groups include alkyl groups having from 1 to 10 carbon atoms while even more preferred such groups have from 1 to 5 carbon atoms. Most preferred alkyl groups include straight and branched chain alkyl groups having from 1 to 3 carbon atoms and include methyl, ethyl, propyl, and —CH(CH$_3$)$_2$. Alkyl groups can further be substituted as defined above.

The phrase "alkylene" refers to divalent straight, branched chain or cyclic alkyl groups having 1 up to about 20 carbon atoms, preferably 2-10 carbon atoms. "Substituted alkylene" refers to alkylene groups which can be substituted as defined above.

The phrase "alkenyl" refers to monovalent straight, branched chain or cyclic hydrocarbyl groups having at least one carbon=carbon double bond, and having 2 up to about 20 carbon atoms, preferably 2-10 carbon atoms. Alkenyl groups can further be substituted as defined above.

The phrase "alkenylene" refers to divalent straight, branched, or alkenyl groups, as defined above, having in the range of about 2 up to 20 carbon atoms. "Substituted alkenylene" refers to alkenylene groups which can be substituted as defined above.

The phrase "alkynyl" refers to monovalent straight, branched chain, or cyclic hydrocarbyl groups having at least one carbon≡carbon triple bond, and having 2 up to about 20 carbon atoms, preferably 2-10 carbon atoms. Alkynyl groups can further be substituted as defined above.

The phrase "alkynylene" refers to divalent straight, branched, or cyclic alkynyl groups, as defined above, typically having in the range of about 2 up to 20 carbon atoms. "Substituted alkynylene" refers to alkynylene groups which can be substituted as defined above.

The phrase "alkylamino" refers to alkyl groups comprising a nitrogen atom. Alkylamino groups can comprise any level of nitrogen substitution, e.g. primary, secondary, or tertiary. Alkylamino groups may be further substituted as defined above.

The phrase "alkyldiamino" refers to alkyl groups comprising two nitrogen atoms. Alkyldiamines can comprise any level of nitrogen substitution, e.g. primary, secondary, or tertiary. Alkyldiamino groups may be further substituted as defined above.

The phrase "alkylcarboxylate" refers to alkyl groups comprising —C(O)O$^-$ or —C(O)OH. Representative alkylcarboxylate groups can be of the formula RCOOH, wherein R is an alkyl group as defined above.

The phrase "alkylamido" refers to alkyl groups comprising an amide functionality of the following forrula: —C(O)NRR' wherein R and R' are independently selected from hydrogen, acetyl, alkyl, alkenyl, alkynyl, and the like. Alkylamido groups may be further substituted as defined above.

The phrase "alkyldiamido" refers to alkyl groups comprising two amide functionalities of the following formula: —C(O)NRR' wherein R and R' are independently selected from hydrogen, acetyl, alkyl, alkenyl, alkynyl, and the like. Alkyldiamido groups may be further substituted as defined above.

The phrase "aminoalkylamido" refers to an alkylamino group, as defined above, further comprising an amide functionality of the following formula: —C(O)NRR' wherein R and R' are independently selected from hydrogen, acetyl, alkyld alkenyl, alkynyl, and the like. Aminoalkylamido groups may be further substituted as defined above. A representative aminoalkylamido group is of the formula —C(O)NH(CH$_2$CH$_2$CH$_2$)N(CH$_3$)$_2$.

The phrase "aminoalkvidiamido" refers to an alkylamino group, as defined above, further comprising two amide functionalities of the following formula: —C(O)NRR' wherein R and R' are independently selected from hydrogen, acetyl, alkyl alkenyl, alkynyl, and the like. Aminoalkyldiamido groups may be further substituted as defined above. A representative aminoalkyldiamide group is of the formula —C(O)NH(CH$_2$CH$_2$)C(O)NH(CH$_2$CH$_2$CH$_2$)N(CH$_3$)$_2$.

Embodiments of the invention include oligomeric backbones containing C—C linked heteromonocyclic/heterobicyclic moiety as shown in Structure (IV) where X is —NR$_3$ wherein R$_3$ is C$_1$-C$_6$ alkyl, such as —CH$_3$; where Z is —CR$_2$ wherein R$_2$ is —OH or H; where Z is N; where V is N; where T is —CR$_1$ wherein R$_1$ is H or —OH; where T is N; where Y is —CR$_1$ wherein R$_1$ is H.

An embodiment is drawn to compounds of the invention further comprising a detectable label. The phrase "detectable label" refers to any moiety which can be observed to facilitate detection of compounds of the invention. Detectable labels include, for example, isotopes, fluorescent moieties, chemiluminescent moieties, magnetic moieties, and dyes.

In an aspect of the invention, compounds of Formula (V) may be capable of binding to dsDNA in a sequence specific manner under physiological conditions. Such DNA-binding polymers form high affinity complexes (i.e., K$_a$ ranging from about 10$^7$ to about 10$^{10}$ M$^{-1}$, such as about 10$^7$, 10$^8$, 10$^9$, or 10$^{10}$, with dsDNA at predetermined sequences. The phrase "binding to dsDNA in a sequence specific manner" refers to the ability of a compound to form at least one complementary pair with at least one DNA specific pair on a dsDNA target sequence. Compounds of the invention can comprise two equal length chains of monomer elements connected by a linker, wherein each monomeric element of each chain binds to a specific nucleotide. Thus, a pair of monomer elements can bind to a specific, complementary pair of nucleotides. For instance, the Ip/Py pair has sequence specificity for G·C; the Bi/Py pair has sequence specificity for T·A and/or A·T; the Hz/Py pair has sequence specificity for T·A; the Py/Hz pair has sequence specificity for A·T; the Hz/Bi pair has sequence specificity for T·A; the Bi/Hz pair having sequence specificity for A·T. Accordingly, consecutive pairs of monomer elements of the compound can bind to a specific DNA sequence on dsDNA. The number of binding pairs contained in compounds of the invention that can bind to specific dsDNA sequences can range from 1 to 10. In other embodiments, the number of binding pairs can range from 2 to 8. In yet other embodiments, the number of binding pairs can range from 4 to 6. Furthermore, in certain embodiments, compounds of the invention may bind specific sequences which are located in the minor groove of dsDNA. It is generally understood by those skilled in the art that the basic structure of DNA in a living cell includes both major and minor grooves. For the purposes of describing the present invention, the minor groove is the narrow groove of DNA as illustrated in common molecular biology reference such as Lewin, B., Genes VI, Oxford University Press, New York (1997).

Compounds of the invention may be brought together with dsDNA under a variety of physiological conditions. Physiological conditions are conditions which occur in vitro, in cell cultures, ex vivo or in vivo. Generally, the pH level in physiological conditions ranges from about 6.5 to 9, and the temperature ranges from about 4° C. to 45° C. Preferable physiological conditions are pH levels of 7-8 and temperatures of 37-42° C.

The phrase "hairpin oligomer backbone" refers to two chains of monomer elements that are linked to each other by a covalent linker L of Structure (V). In a hairpin oligomer backbone, the linker which covalently links the two chains imparts an overall U-turn shape to the oligomer backbone. Hairpin oligomers are well known in the art and are described, for example, in Church et al., *Biochemistry* 29: 6827, 1990, and He et al., *JACS* 115: 7061, 1993.

The phrase "five-membered heterocycle" refers to a cyclic ring of five atoms, wherein at least one atom of the ring is a heteroatom. The five-membered heterocycle can be aromatic or non-aromatic. An example of a five-membered heterocycle is

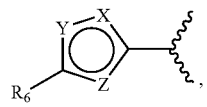

wherein each of X, Y and Z is independently —CR$_2$, N, —NR$_3$, O, or S and R$_6$, wherein R$_6$ is independently H, halogen, NO, N-acetyl, CHO, benzyl, C$_1$-C$_{12}$ alkyl, C$_2$-C$_{12}$ alkenyl, C$_2$-C$_{12}$ alkynyl, C$_1$-C$_{12}$ alkylamino, C$_1$-C$_{12}$ alkyldiamino, C$_1$-C$_{12}$ alkylamido, C$_1$-C$_{12}$ alkyldiamido, C$_1$-C$_2$ aminoalkylamido, C$_1$-C$_{12}$ aminoalkyldiamido, C$_1$-C$_{12}$ alkylcarboxylate, or a covalent bond; and wherein each of R$_2$ and R$_3$ is independently H, halogen, —OH, —OMe, —SH, —CN, —OAc, —NH$_2$, —NHAc, C$_1$-C$_6$ alkyl, C$_1$-C$_6$ alkylamino, C$_1$-C$_6$ alkenyl, or C$_1$-C$_6$ alkynyl. For instance, representative five-membered heterocycles include N-methyl pyrrole (Py), N-methyl imidazole (Im), 3-hydroxypyrrole (Hp), furan (Fr), 5-methylthiazole (Nt), 1-methyl-1H-pyrazole (Pz), 3-hydroxythiopene (Ht), pyrrole, triazole, thiophene, oxazole, and the like. Preferred five-membered heterocycles include N-methylpyrrole (Py), 1-methyl-1H-pyrazole (Pz), 1H-pyrrole (Nh), N-methyl imidazole (Im), 5-methylthiazole (Nt), furan (Fr), 3-hydroxypyrrole (Hp), 3-hydroxythiopene (Ht), 4-methylthiazole (Tb), 3-methylthiophene (Tn), and thiophene (Tp).

The phrase "fused six-membered cyclic monomer" or "used six-membered ring" refers to a ring of six atoms which is fused to another ring structure. Preferably, at least one atom in either ring structure is a heteroatom. Fused six-membered rings include 6-5 ring systems wherein both rings are aromatic. An example of a fused six-membered ring is

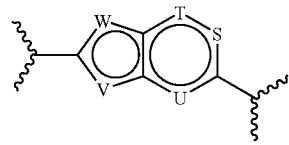

wherein each of S, T, and U is independently —CR$_1$ or N and each of V and W is independently —CR$_2$, N, —NR$_3$, O, or S, wherein each R$_1$ is independently H, halogen, —OH, —OMe, —OAc, —NH$_2$, —NHAc, —CH$_3$, —SH, —NO$_2$, —CHO, —SO$_2$H, —S(O)NH$_2$, —C=C)(CN)$_3$, —CN, acetyl, C$_1$-C$_6$-alkyl, or C$_1$-C$_6$-alkylamino; and each of R$_2$ and R$_3$ is independently H, halogen, —OH, —OMe, —SH, —CN, —OAc, —NH$_2$, —NHAc, C$_1$-C$_6$-alkyl, C$_1$-C$_6$-alkylamino, C$_2$-C$_6$-alkenyl, or C$_2$-C$_6$-alkynyl. For instance, representative fused six-membered rings include benzimidazole (Bi), imidazo[4, 5-b]pyridine (Ip), and hydroxybenzimidazole (Hz). Preferred fused six-membered cyclic monomers, include benzimida zole (Bi), imidazo[4,5-b]pyridine (Ip), and hydroxybenzimidazole (Hz), structures of which are shown below:

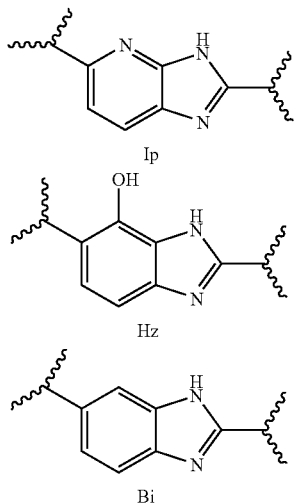

Each monomer element can be attached to another monomer element, first terminus, second terminus or optional linking element by a connectivity denoted as B, wherein B is independently

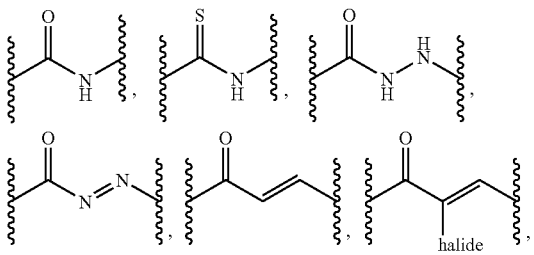

or a direct bond. The connectivity between each monomer element in the present backbone oligomers may be the same or different throughout the backbone oligomer. Preferable connectivity for monomer elements of the invention are the amide bond, —C(=O)NH—, which gives rise to polyamide backbone oligomers and the direct bond.

The phrase "linker" refers to an optionally substituted aliphatic moiety comprising 2 to 12 carbon atoms which links, joins, attaches, or connects two equal length oligomeric backbone chains to form in combination with the aforementioned termini compounds of the invention. Representative linkers which can be used in the present compounds include $C_{2-6}$-alkylene, $C_{2-6}$ alkyleneamino, and aliphatic amino acids (connecting the chains via the amino and carboxyl terminal ends). For instance, exemplary linkers include aminopropylene, —CH$_2$CH$_2$CH$_2$—, β-alanine, gamma-aminobutyric acid, or diaminobutyric acid (DAB). Preferred linkers include gamma-aminobutyric acid and diaminobutyric acid.

The present invention also provides methods for preparing an oligomeric backbone in covalent linkage with a thiophene-containing terminus. Methods presented herein comprise attaching an amino protected polyamide monomer to a prepared resin; coupling another amino protected monomer to form an oligomer; and optionally, repeating the coupling step with another amino protected monomer to form an oligomer of a desired length, and ultimately terminating the growing chain with covalent addition of the thiophene-containing terminus.

The phrase "prepared resin" refers to standard resins used in routine peptide coupling procedures which are prepared for use in heterocyclic coupling. Standard resins include, for example, Kaiser's oxime resin, which may be used to prepare oligomers of the invention. Stepwise coupling of amino protected monomer elements to form backbone oligomers is a well known procedure in the art and is described, for example, in Baird, E. E., *J. Am. Chem. Soc.* 118, 61141-6146, 1996.

The phrase "protected amino group" refers to standard moieties used to protect reactive amines, e.g. amino protecting groups. Heterocyclic and aliphatic monomers can be protected with a variety of standard amino protecting groups, such as t-butoxycarbonyl (Boc) and 9-fluorenylmethoxycarbonyl (Fmoc), for instance.

The phrase "reactive carboxyl group" refers to standard moieties used to activate carboxyl groups, e.g. via carboxyl activating agents. Heterocyclic monomers comprising a carboxyl group substituent may be activated by a variety of standard activating agents, such as N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP), bis(2-oxo-3-oxazolidinyl)phosphine chloride (BOPCl), and the like.

The present invention also provides methods for forming specific complexes between target dsDNA and DNA-binding polymer compounds of the invention. By contacting dsDNA with a DNA-binding polymer that is capable of binding to a specific sequence on said dsDNA, specific complexes can be formed between the DNA-binding polymer and a target sequence on dsDNA. In certain embodiments, DNA-binding polymers which form specific complexes with target dsDNA further comprise at least one five-membered heterocycle independently selected from the group consisting of Py, Im, Hp, Fr, Nt, Pz, Ht, pyrrole, triazole, thiophene, and oxazole.

The present invention also provides methods for detecting the presence of a specific sequence in a sample comprising dsDNA by contacting the sample with a DNA-binding polymer comprising at least one fused six-membered ring and a detectable label. By contacting dsDNA with a DNA-binding polymer that is capable of binding to a specific sequence on said dsDNA, specific complexes can be formed between the DNA-binding polymer and a target sequence on dsDNA. The detectable label on the DNA-binding polymer can be observed from the specific complexes, indicating the presence of a specific sequence. In certain embodiments, DNA-binding polymer which form specific complexes with target dsDNA further comprise at least one five-membered heterocycle.

The present invention also provides methods for isolating target dsDNA from a sample comprising a mixture of dsDNA by contacting the sample with a DNA-binding polymer. By contacting dsDNA with a DNA-binding polymer that is capable of binding to a specific sequence on said dsDNA, specific complexes can be formed between the DNA-binding polymer and a target sequence on dsDNA. The target dsDNA can then be isolated from the specific complex. In certain embodiments, DNA-binding polymers which form specific complexes with target dsDNA further comprise at least one thiophene-containing terminus.

The present invention also provides methods for modulating transcription of a target gene in a cell by contacting the cell with an effective amount of a DNA-binding polymer comprising at least one thiophene-containing terminus. By contacting dsDNA with a polyamide oligomer that is capable of binding to a specific sequence on said target gene, such as sequences on transcriptional regulatory regions of said gene, specific complexes can be formed between the polyamide oligomer and the target gene. Formation of polyamide complexes at sequences on the target gene can modulate transcription of that gene, particularly when complexes are formed at transcriptional regulatory regions of the gene. In certain embodiments, polyamide oligomers which form specific complexes with the target gene further comprise at least one five-membered heterocycle. In certain embodiments, the cell is eukaryotic, such as a mammalian cell, as in a human cell. In other embodiments, the cell is prokaryotic, such as a bacterial cell. In certain embodiments, the target gene is any gene implicated in the manifestation or propagation of a disease state. For example, the target gene is viral or is an oncogene. In certain embodiments, the cell is in a subject, such as a mammal, as in a human.

The phrase "effective amount" refers to an amount of polyamide oligomer that is effective in achieving a desired effect for a particular application. Effective amounts can vary depending upon the specific polyamide oligomer and the accessibility of the sequence on dsDNA. Generally, ranges of amounts of polyamide oligomer effective in reducing transcription of a target gene in a cell are 1 pM-50 mM, such as 1 nM-100 µM, such as about 30 nM.

The present invention also provides methods for treating cancer by reducing the level of transcription of a target oncogene by administering to a subject an effective amount of a polyamide oligomer which comprises at least one fused six-membered ring. By contacting dsDNA with a polyamide oligomer that is capable of binding to a specific sequence on said oncogene, specific complexes can be formed between the polyamide oligomer and a target oncogene on dsDNA. Formation of polyamide complexes at specific sequences on the target oncogene reduces transcription of that oncogene, such as when complexes are formed at transcriptional regulatory regions of the oncogene. In certain embodiments, polyamide oligomers which form specific complexes with the target oncogene further comprise at least one thiophene-containing terminus. In certain embodiments, the subject is a mammal, such as a human.

Kits comprising compounds of the invention and compositions comprising compounds of the invention and a pharmaceutically acceptable carrier are also presented. Compounds of the invention may be used for detection or isolation of specific sequences in a sample of dsDNA. Furthermore, compounds of the invention may be used to reduce transcription of a target gene, such as an oncogene, in a cell.

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (2000); Goeddel, D., ed., Gene Expression Technology, *Methods in Enzymology*, 185, Academic Press, San Diego, Calif. (1991); "Guide to Protein Purification" in Deutshcer, M. P., ed., Methods in Enzymology, Academic Press, San Diego, Calif. (1990); Innis, et al., *PCR Protocols: A Guide to Methods and Applications*, Academic Press, San Diego, Calif. (1997); Freshney, R. I., *Culture of Animal Cells. A Multimedia Guide*, Fourth Edition, Alan Liss, Inc. New York, N.Y. (April 2000); Murray, E. J., ed., "*Gene Transfer and Expression Protocols*", pp. 109-128, The Human Press Inc., Clifton, N.J. and Lewin, B., Genes VI, Oxford University Press, New York (April 1991).

Preparation of Compounds of the Invention

Methods for preparing monomer elements comprising five-membered heterocycles as shown above are well known to one of skill in the art, and can be accomplished by a variety of standard methods, as described in, for example, Minehan et al., *Helvetica Chimica Acta* 85: 4485-4517, 2002. Exemplary synthetic schemes for the preparation of thiophene containing reagents and compounds of the invention are illustrated below in the Examples.

Methods for preparing monomer elements comprising fused six-membered heterocycles are well known to one of skill in the art, and can be accomplished by a variety of standard methods, as described in, for example, Renneberg et al., *JACS* 125, 5707-5716, 2003 and Briehn et al., *Chem. Eur. J.* 9: 2110-2112, 2003. Exemplary synthetic schemes for the preparation of representative fused six-membered heterocycles are illustrated below in the Examples.

Compounds of the present invention can be synthesized by a variety of well known synthetic methods, such as solid phase synthesis, as described in, for example, Renneberg et al., supra and Briehn et al., supra. Exemplary synthetic schemes for the preparation of representative oligomers of the invention are illustrated below in the Examples.

Compounds of the invention can be purified by a sequence of chromatographic steps employing any or all of the following types: ion exchange on a weakly basic resin (acetate form); hydrophobic adsorption chromatography on underivitized polystyrene-divinylbenzene (for example. Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Oligomers of a desired length are removed from the resin and deprotected, either successively or in a single operation, using well known procedures. For instance, deprotection of amino protecting groups can be accomplished with acidic solutions, such as 20% trifluoroacetic acid (TFA) or 50% TFA in methylene chloride. Liberation of the oligomer may be accomplished by a variety of well known methods, such as treatment with a warm solvent solution (approximately 37° C.), such as tetrahydrofuran (THF) or methylamine in methylene chloride for 8-24 hrs. Oligomers may be used directly after cleavage from the resin or can be further purified using a variety of well known purification methods, such as reverse-phase HPLC. The identity and purity of the polyamides may be verified using any of a variety of analytical techniques available to one skilled in the art such as $^1$H-NMR, analytical HPLC, and/or matrix-assisted laser-desorption ionization time-of-flight mass spectrometry (MALDI-TOF MS-monoisotropic).

Specific Binding of DNA Pairs by Compounds of the Invention

In an aspect of the invention, compounds of the invention are capable of binding to dsDNA in a sequence specific manner. Presented herein are novel binding pairs which recognize specific nucleotide base pairs. Table 2 below lists the pairing rules for binding pairs comprising six-membered heterocycles.

TABLE 2

Specific DNA Recognition of Pairs Comprising Fused Six-Membered Rings

| Representative Six-Membered Pair | DNA Pair(s) Recognized |
| --- | --- |
| Ip/Py | G•C |
| Bi/Py | T•A |
|  | A•T |
| Hz/Py | T•A |
| Py/Hz | A•T |
| Hz/Bi | T•A |
| Bi/Hz | A•T |

Recognition of specific sequences on dsDNA by certain polyamide pairs comprising six-membered rings at subnanomolar concentrations are described in Renneberg et al., step a and Briehn et al., supra. Application of the novel polyamide pairs listed above in Table 2 can be used in conjunction with previously described polyamide five-membered heterocyclic pairs towards the construction of a wide array of versatile polyamide oligomers. Experimental data illustrating sequence specific recognition of representative oligomers of the invention is provided below in the Examples.

Oligomers of the invention provide for targeting of predetermined DNA sequences, based on pairing rules shown in Tables 1 and 2, with high affinity and specificity. By employing the binding pairs listed above, oligomers of the invention may be designed to bind to any target DNA sequence.

Detection and Isolation Methods Using Oligomers of the Invention

The formation of complexes between dsDNA and the DNA-binding polymers of the present invention may be used for diagnostic, therapeutic, purification, research purposes, and the like. DNA-binding polymers of the present invention can be used to detect specific dsDNA sequences in a sample without melting the dsDNA. Examples of diagnostic applications for which DNA-binding polymers of the present invention may be used include detection of alleles, identification of mutations, identification of a particular host, e.g. bacterial strain or virus, identification of the presence of a particular DNA rearrangement, identification of the presence of a particular gene, e.g. multiple resistance gene, forensic medicine, or the like. With pathogens, the pathogens may be viruses, bacteria, fungi, protista, chlamydia, or the like. With higher hosts, the hosts may be vertebrates or invertebrates, including insects, fish, birds, mammals, and the like or members of the plant kingdom.

DNA-binding polymers of the present invention are also useful for detecting the presence of dsDNA of a specific sequence for diagnostic or preparative purposes. The sample containing the dsDNA can be contacted by a DNA-binding polymer linked to a solid substrate, thereby isolating DNA comprising a desired sequence. Alternatively, DNA-binding polymers linked to a suitable detectable marker, such as biotin, a hapten, a radioisotope or a dye molecule, can be contacted by a sample containing double stranded DNA.

For instance, one may wish to have an isotopic DNA-binding polymer which can be detected through various well known methods, such as via scintillation counters and nuclear magnetic resonance spectroscopy, and the like. A radioactive moiety may be employed as a detectable label, such as tritium, $^{14}C$, $^{125}I$, or the like. The radiolabel may be a substituent on a carbon or a heteroatom or any atom in any monomer, or the radiolabel may be a substituent at either terminus of the DNA-binding polymer. The radiolabel may serve numerous purposes in diagnostics, cytohistology, radiotherapy, and the like.

Other detectable labels include fluorescers, e.g. dansyl, fluorescein, Texas red, isosulfan blue, ethyl red, and malachite green, chemiluminescers, magnetic particles, colloidal particles, gold particles, light sensitive bond forming compounds, i.e. psoralens, anthranilic acid, pyrene, anthracene, and acridine, chelating compounds, such as EDTA, NTA, tartaric acid, ascorbic acid, polyhistidines of from 2 to 8 histidines, alkylene polyamines, etc., chelating antibiotics, such as bleomycin, where the chelating compounds may chelate a metal atom, such as iron, cobalt, nickel, technetium, etc., where the metal atom may serve to cleave DNA in the presence of a source of peroxide, intercalating dyes, such as ethidium bromide, thiazole orange, thiazole blue, TOTO, 4',6-diamidino-2-phenylindole (DAPI), etc., enzymes, such as β-galactosidase, NADH or NADHP dehydrogenase, malate dehydrogenase, lysozyme, peroxidase, luciferase, etc., alkylating agents such as haloacetamides, N-ethyl nitrosourea, nitrogen and sulfur mustards, sulfonate esters, etc., and other compounds, such as arylboronic acids, tocopherols, lipoic acid, camptothecin, etc. colloidal particles, e.g., gold particles, fluorescent particles, peroxides, DNA cleaving agents, oligonucleotides, oligopeptides, NMR agents, stable free radicals, metal atoms, etc. The DNA-binding polymer may be combined with other labels, such as haptens for which a convenient receptor exists, e.g. biotin, which may be complexed with avidin or streptavidin and digoxin, which may be complexed with antidigoxin, etc. where the receptor may be conjugated with a wide variety of labels, such as those described above. The DNA-binding polymers may be joined to sulfonated or phosphonated aromatic groups, e.g. naphthalene, to enhance inhibition of transcription, particularly of viruses (Clanton et al., *Antiviral Res.*, 27:335-354, 1995). In some instances, one may bond multiple copies of the subject DNA-binding polymers to polymers, where the subject DNA-binding polymers are pendant from the polymer. Polymers, particularly water soluble polymers, which may find use are cellulose, poly(vinyl alcohol), poly(vinyl acetate-vinyl alcohol), polyacrylates, and the like.

For detecting the presence of a target sequence, the dsDNA may be extracellular or intracellular. When extracellular, the dsDNA may be in solution, in a gel, on a slide, or the like. The dsDNA may be present as part of a whole chromosome or fragment thereof of one or more centiMorgans. The dsDNA may be part of an episomal element. The dsDNA may be present as smaller fragments ranging from about 20, usually at least about 50, to a million base pairs, or more. The dsDNA may be intracellular, chromosomal, mitochondrial, plastid, kinetoplastid, or the like, part of a lysate, a chromosomal spread, fractionated in gel elecrophoresis, a plasmid, or the like, being an intact or fragmented moiety. When involved in vitro or ex vivo, the dsDNA may be combined with the subject compositions in appropriately buffered medium, generally at a concentration in the range of about 0.1 nM to 1 mM. Various buffers may be employed, such as TRIS, HEPES, phosphate, carbonate, or the like, the particular buffer not being critical to this invention. Generally, conventional concentrations of buffer will be employed, usually in the range of about 10-200 mM. Other additives which may be present in conventional amounts include sodium chloride, generally from about 1-250 mM, dithioitreitol, and the like, the particular nature or quanititv of salt not being critical to this invention. The pH will generally be in the range of about 6.5 to 9, the particular pH not being critical to this invention. The temperature will generally be in a range of 4-45° C., the particular temperature not being critical to this invention. The target dsDNA may be present in from about 0.001 to 100 times the moles of DNA-binding polymer.

The present invention also provides a diagnostic system, preferably in kit form, for assaying for the presence of the double stranded DNA sequence bound by DNA-binding polymers of the invention in a body sample, such as brain tissue, cell suspensions or tissue sections, or body fluid samples such as colony stimulating factor (CSF), blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific DNA-binding polymer as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated DNA-binding polymer or it can be a microliter plate well to which microgram quantities of a contemplated DNA-binding polymer have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated DNA-binding polymer of the present invention to the target DNA sequence. As noted above, numerous detectable labels, such as biotin, and detecting or indicating means, such as enzyme-linked (direct or indirect) streptavidin, are well known in the art.

Kits may optionally contain instructions for administering DNA-binding polymers or compositions of the present invention to a subject having a condition in need of treatment. Kits may also comprise instructions for approved uses of DNA-binding polymers of the invention by regulatory agencies, such as the United States Food and Drug Administration. Kits may optionally contain labeling or product inserts for DNA-binding polymers of the invention. The package(s) and/or any product insert(s) may themselves be approved by regulatory agencies. The kits can include DNA-binding polymers of the invention in the solid phase or in a liquid phase (such as buffers provided) in a package. The kits also can include buffers for preparing solutions for conducting the methods, and pipettes for transferring liquids from one container to another.

Representative Target Sequences on dsDNA

In an aspect of the invention, DNA-binding polymers bind dsDNA in a sequence specific manner at any pre-determined target sequence. Target sequences can include coding and noncoding DNA sequences. For instance, target sequences can include transcriptional regulatory sequences, such as promoter regions and enhancer regions.

A representative regulatory sequence is 5'-TATAAA-3' also called the "TATA box", which when positioned on the coding strand of DNA approximately 30 base pairs upstream of the transcription start site, forms part of the promoter region (Lewin, Genes VI, pp. 831-835).

An exemplary target sequence for binding with DNA-binding polymers of the invention is a promoter region. As used herein, the term "promoter" refers to a regulatory sequence of DNA that is involved in the binding of RNA polymerase to initiated transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream (5' to) the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogenous ligand (e.g. a transcription factor) to the regulatory sequence increases transcription, thereby resulting in increased expression of the corresponding target gene. In such a case, interference with transcription by binding DNA-binding polymers of the present invention to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a DNA-binding polymer of the invention to prevent binding of a factor to a silencer regulatory sequence or indirectly, by using a DNA-binding polymer to block transcription of a factor to a silencer regulatory sequence.

While not being bound to any hypothesis, it is believed that the binding of DNA-binding polymers of the invention modulate gene expression by altering the binding of DNA binding proteins, such as RNA polymerase, transcription factors, THF, TFIIIB and other proteins. The effect on gene expression of DNA-binding polymer binding to a segment of double stranded DNA is believed to be related to the function, e.g., promoter, of that segment of DNA.

DNA-binding polymers of the present invention may bind to any of the above-described DNA sequences or any other sequence having a desired effect upon expression of a gene. In addition, U.S. Pat. No. 5,578,444 describes numerous promoter targeting sequences from which base pair sequences for targeting a DNA-binding polymer of the present invention may be identified.

Modulation of Expression of Target Genes

To modulate gene expression in a cell, which may include causing an increase or a decrease in gene expression, an effective amount of one or more DNA-binding polymer of the invention is contacted with the cell and internalized by the cell. The cell may be contacted in vivo or in vitro. Effective extracellular concentrations of DNA-binding polymers that can modulate gene expression range from about 10 nanomolar to about 1 micromolar (Gottesfeld, J. M., et al., Nature 387:202-205 (1997)). One exemplary method to determine effective amounts and concentrations of DNA-binding polymers in vitro is to place a suitable number of cells on tissue culture plates and add various quantities of one or more DNA-binding polymers to separate wells. Gene expression following exposure to a DNA-binding polymer can be monitored in the cells or medium by detecting the amount of the protein gene product present as determined by various techniques utilizing specific antibodies, including ELISA and Western blot. Alternatively, gene expression following exposure to a DNA-binding polymer can be monitored by detecting the amount of mRNA present as determined by various techniques, including northern blot and RT-PCR.

An exemplary method to determine effective amounts and concentrations of DNA-binding polymers for in vivo administration involves obtaining a sample of body tissue or fluid, such as plasma, blood, urine, cerebrospinal fluid, saliva, or biopsy of skin, muscle, liver, brain or other appropriate samples to analyze. Gene expression following exposure to a DNA-binding polymer of the invention can be monitored by detecting the amount of the protein gene product present as determined by various techniques utilizing specific antibodies, including ELISA and western blot. Alternatively, gene expression following exposure to a DNA-binding polymer can be monitored by the detecting the amount of mRNA present as determined by various techniques, including northern blot and RT-PCR.

Therapeutic Applications

Compounds of the present invention have utility in the treatment or prevention of disease. It is contemplated that these compounds may be used independently or in conjunction with inactive excipients or active ingredients. As used herein, the term "agent" refers to compounds of the invention or compositions thereof comprising active and/or inactive ingredients.

In an aspect of the invention, DNA-binding polymers of the invention may be used to modulate the expression of a variety of target genes, including any gene which is implicated in the manifestation or propagation of a disease state. For instance, expression of viral genes may be inhibited using DNA-binding polymers of the invention. Exemplary viral genes include HIV, HTLV, HPV, and HSV related genes.

DNA-binding polymers of the invention may also be used to decrease the expression of an oncogene, Aberrant expression of various oncogenes has been implicated in the manifestation of abnormal cellular proliferation. Representative oncogenes wherein expression may be modulated by DNA-binding polymers of the invention include v-sis, int 2, KS3, HST, int-1, EGFR, v-fms, v-kit, v-ros, MET, TRK, NEU, RET, sea, Dbl, Ost, Tiam-1, Vav, Lbc, H-RAS, K-RAS, N-RAS, gsp, gip, v-crk, SRC, v-yes, v-fgr, v-fps, v-fes, BCR/ABL, ros, v-mos, v-raf, pim-1, cot (ser/thr), v-myc, N-MYC, L-MYC, v-myb, v-fos, v-jun, v-ski, v-rel, v-ets, and v-erbA. Accordingly, DNA-binding polymers of the instant invention may be administered to a subject for the treatment or amelioration of cancer. "Treating" as used herein refers to alleviation of at least one symptom associated with cancer, or halt of further progression or worsening of such symptom, or prevention or prophylaxis of cancer.

Delivery Modes

The particular delivery mode selected will depend upon the particular DNA-binding polymer selected, the condition being treated, the severity of the condition, whether the treatment is therapeutic or prophylactic, and the dosage required for efficacy. Therapeutic delivery of DNA-binding polymers of the invention may be practiced using any mode of administration that is medically acceptable, meaning any mode that produces effective levels of the active compounds without causing clinically unacceptable adverse effects. Any dosage forms containing effective amounts are well within the bounds of routine experimentation and therefore, well within the scope of the instant invention. A therapeutically effective dose may vary depending upon the route of administration and dosage form. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the agent in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

Direct administration of DNA-binding polymers of the present invention to a designated site may be preferred for some methods provided herein. For example, treatment with the DNA-binding polymer via topical administration in and around affected areas may be performed. In still other embodiments, DNA-binding polymers may be delivered by injection directly into the tissue with, for example, a biopsy needle and syringe.

Systemic administration may be preferred in some instances such as, for example, if the subject is known to have or is suspected of having metastases. In this way, all tumor sites, whether primary or secondary may receive the DNA-binding polymer. Systemic delivery may be accomplished through for example, oral or parenteral administration. Inhalation may be used in either systemic or local delivery, as described below.

Representative Dosing Regimens

The DNA-binding polymers of the invention are administered in therapeutically effective amounts. A therapeutically effective amount is an amount sufficient to delay the onset of, inhibit the progression of, or halt altogether the particular condition being treated. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. A therapeutically effective dose results in amelioration of at least one undesirable symptom. It is preferred generally that a maximum dose be used, that is, the highest safe dose according to sound medical judgment.

Dosing amounts, dosing schedules, routes of administration and the like can be selected so as to affect bio-activity of the present compounds. Such determinations are routine and well known to one of ordinary skill in the art.

A therapeutically effective amount typically varies from 0.01 mg/kg to about 1000 mg kg, preferably from about 0.1 mg/kg to about 200 mg/kg, and most preferably from about 0.2 mg/kg to about 20 mg/kg, in one or more dose administrations daily, for one or more days. In some embodiments, the DNA-binding polymers are administered for more than 7 days, more than 10 days, more than 14 days and more than 20 days. In still other embodiments, the agent is administered over a period of weeks, or months. In still other embodiments, the agent is delivered on alternate days. For example, the agent is delivered every two days, or every three days, or every four days, or every five days, or every six days, or every week, or every month.

DNA-binding polymers of the invention can also be administered in prophylactically effective amounts. In these instances, the DNA-binding polymers are administered in an amount effective to prevent the development of an abnormal or undesirable condition or disease. For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow or halt the development of or the progression of a cell mass such as, for example, a tumor. As used in the embodiments, "inhibit" embraces all of the foregoing.

For example, in connection with methods directed to inhibition of mammalian cell proliferation, a therapeutically effective amount will be an amount necessary to extend the dormancy of micrometastases or to stabilize any residual primary tumor cells following surgical or drug therapy.

Pharmaceutically Acceptable Carriers

Compositions presented herein may include DNA-binding polymers of the invention in combination with any standard physiologically and/or pharmaceutically acceptable carrier known in the art. The term "pharmaceutically acceptable carrier" as used herein means one or more compatible solid or liquid fillers, diluents or encapsulating substances which are suitable for administration to a subject. The term "carrier" denotes an organic or inorganic ingredient, natural or synthetic, which with the DNA-binding polymer is combined to facilitate delivery of the composition. The components of the pharmaceutical compositions also are capable of being co-mingled with the molecules of the present invention, and with each other, in a manner so as to not substantially impair the desired pharmaceutical efficacy. Pharmaceutically acceptable further means a non-toxic material that is compatible with a biological system such as a cell, cell culture, tissue, or organism. The particular carrier may vary depending on the route of therapeutic delivery.

Pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or DNA-binding polymers of the instant invention can also be administered in a local rather than a systemic fashion, such as injection as a sustained release formulation. The following dosage forms are given by way of example and should not be construed as limiting the instant invention.

Compositions suitable for parenteral administration conveniently comprise a sterile aqueous preparation of the agent, which is preferably isotonic with the blood of the recipient.

This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. Administrations can be found, for example, in "Remington's Pharmaceutical Sciences" Mack Publishing Co., New Jersey (1991), which is incorporated herein by reference.

Preparations for parenteral administration include sterile aqueous or non-aqueous solutions, suspensions, and emulsions Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, lozenges, each containing a predetermined amount of the agent. Other compositions include suspensions in aqueous liquids or non-aqueous liquids such as a syrup, elixir or an emulsion. Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

Compositions may comprise a biocompatible micropar-ticle or implant that is suitable for implantation. Biocompatible and biodegradable polymeric matrix materials may also be added. The polymeric matrix may be used to achieve sustained release of the agent in a subject. DNA-binding polymers of the invention may be encapsulated or dispersed within a biocompatible and biodegradable polymeric matrix. The polymeric matrix can be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Such polymers may be natural or synthetic polymers. Synthetic polymers are preferred. The polymer is selected based on the period of time over which release is desired, generally in the order of a few hours to a year or longer. The polymer optionally is in the form of a hydrogel that can absorb up to about 90% of its weight in water and further, optionally is cross-linked with multi-valent ions or other polymers.

Exemplary synthetic polymers which can be used include: polyamides, polycarbonates, polyalkylenes, polyalkylene glycols, polyalkylene oxides, polyalkylene terpthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers may also be included in the present compositions. Examples of such bioadhesive polymers include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Compositions of the present invention may be formulated as timed release, delayed release, or sustained release delivery systems. Such systems can avoid the need for repeated administrations of the agent of the invention, increasing convenience to the subject and the physician. Many types of release delivery systems are available and known to those of ordinary skill in the art. They include the above-described polymeric systems, as well as polymer base systems such as poly(lactide-glycolide), polyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be used in the treatment of chronic conditions, such as the suspected presence of dormant metastases. Long-term release, are used herein, means that the implant is constructed and arranged to deliver therapeutic levels of the active ingredient for at least 30 days, at least 60 days and more preferably for several months.

Long-term sustained release implants are well-known to those of ordinary skill in the art and include some of the release systems described above.

For oral, buccal, and sublingual administration, powders, suspensions, granules, tablets, pills, capsules, gelcaps, and caplets are acceptable as solid dosage forms. These can be prepared, for example, by mixing one or more DNA-binding polymers of the instant invention, or pharmaceutically acceptable salts or tautomers thereof, with at least one additive or excipient such as a starch or other additive. Suitable additives or excipients are sucrose, lactose, cellulose, sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents, or perfuming agents. Additionally, dyestuffs or pigments may be added for identification. Tablets and pills may be further treated with suitable coating materials known in the art.

As noted above, suspensions may include oils. Such oils include, but are not limited to, peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or DNA-binding polymers of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or diluents include sterilized water, Ringer's solution, or an isotonic aqueous saline solution.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more DNA-binding polymers of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Representative Pharmaceutically Acceptable Salts

Compositions of the present invention embrace pharmaceutically acceptable salts of DNA-binding polymers of the invention. Pharmaceutically acceptable salts include a salt with an inorganic base, organic base, inorganic acid, organic acid, or basic or acidic amino acid. As salts of inorganic bases, the invention includes, for example, salts of alkali metals (such as sodium or potassium) and alkaline earth metals (such as calcium and magnesium or aluminum, and ammonia). As salts of organic bases, the invention includes, for example, salts of trimethylamine, triethylamine, pyridine, picoline, ethanolamine, diethanolamine, triethanolamine. As salts of inorganic acids, the instant invention includes, for example, salts of hydrochloric acid, hydroboric acid, nitric acid, sulfuric acid, and phosphoric acid. As salts of organic acids, the instant invention includes, for example, salts of formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

The following examples are provided to further illustrate aspects of the invention These examples are non-limiting and should not be construed as limiting any aspect of the invention.

EXAMPLES $^1$H NMR and $^{13}$C NMR spectra were recorded on a Varian Mercury 300 and 500 instrument. Chemical shift values were recorded as parts per million relative to solvent and coupling constants in hertz. All NMR spectra were measured at room temperature (unless otherwise stated). UV spectra were measured on a Beckman Coulter DU 7400 diode array spectrophotometer. Mass spectra were recorded on the following mass spectrometer: matrix-assisted, laser desorption/ionization time-of-flight (MALDI-TOF) on Voyager DE-PRO from Applied Biosystems, fast atom bombardment (FAB) on a JEOL JMS-600H double focusing high-resolution magnetic sector, and electrospray injection (ESI) LCQ ion trap on a LCQ classic, Thermofinnigan and were carried out at the Protein and Peptide Microanalytical Facility at the California Institute of Technology.

Precoated plates silica gel 60F$_{254}$ (Merck) were used for TLC and silica gel 60 (40 µm) for flash chromatography. Visualization was realized by UV and/or by using a solution of Ce(SO$_4$)$_2$, phosphomolybdic acid, H$_2$SO$_4$, and H$_2$O. HPLC analysis was performed on a Beckman Gold system (using, for example, a Varian C$_{18}$, Microsorb-MV 100-5, 250×4.6 mm reversed-phase column or a RAININ C18, Microsorb MV, 5 µm, 300×4.6 mm reversed-phase column) in 0.1% (w/v) TFA with acetonitrile as eluent and a flow rate of 1.0 mL/min, gradient elution 1.25% acetonitrile/min. Preparatory HPLC was carried out on a Beckman HPLC using a Waters DeltaPak 100×25 mm, 100 µm C$_{18}$ column, 0.1% (w/v) TFA, 0.25% acetonitrile/min. 18MΩ water was obtained from a Millipore MilliQ water purification system, and all buffers were 0.2 µm filtered.

DNA oligonucleotides were synthesized by the Biopolymer Synthesis Center at the California Institute of Technology and used without further purification. Plasmids were sequenced by the Sequence/Structure Analysis Facility (SAF) at the California Institute of Technology. DNA manipulations were performed according to standard protocols. Autoradiography was performed with a Molecular Dynamics Typhoon Phosphorimager. Reactions were carried out under Arm anhydrous solvents. N,N'-Dicyclohexyl-carbodiimide (DCC), N-hydroxybenzotriazole (HOBt), and 2-(1H-benzotriazole-1-yl)-1,1,3,3-tetramethyluronium hexafluorophosphate (HBTU) were purchased from Peptides International. Oxime resin was purchased from Novabiochem (0.48 mmol/g). (R)-2-Fmoc-4-Boc-diaminobutyric acid (α-Fmoc-γ-Boc-(R)-DABA) was from Bachem, N,N-Diisopropylethylamine (DIEA) and N,N-dimethylformamide (DMF) were purchased from Applied Biosystems, methyl 3,4-diaminobenzoate (19) from Avocado, dichloromethane (DCM) was reagent grade from EM, and trifluoroacetic acid (TFA) was from Halocarbon. Bis(triphenylphosphine)palladium-(II) dichloride was from Fluka, all other reagents were from Aldrich (highest quality available). All enzymes (unless otherwise stated) were purchased from Roche Diagnostics and used with their supplied buffers. pUC19 was from New England Biolabs, [α-$^{32}$P]-Deoxyadenosine triphosphate and [α-$^{32}$P]-thymine triphosphate was purchased from New England Nucleotides. RNase-free water (used for all DNA manipulations) was from US Biochemicals, Ethanol (200 proof) was from Equistar, 2-propanol from Mallinckrodt, Premixed tris-borate-EDTA (Gel-Mate, used for gel running buffer) was from Gibco. Bromophenol blue and xylene cyanol FF were from Acros. 3-Methoxy-1-methyl-4-nitro-1H-pyrrole-2-carboxylic acid was synthesized as reported earlier (Briehn, C. A.; Weyermann, P.; Dervan, P. B. *Eur. J. Chem.*, in press).

dNTPs (PCR nucleotide mix) and all enzymes (unless otherwise stated) were purchased from Roche Diagnostics and used with their supplied buffers, pUC19 was from New England Biolabs, [α-$^{32}$P]-Deoxyadenosine triphosphate and [α-$^{32}$P]-thymine triphosphate was from New England Nucleotides. RNase-free water (used for all DNA manipulations) was from US Biochemicals. Ethanol (100%) was from Equistar, isopropanol from Mallinckrodt. Bromophenol blue and xylene cyanol FF were from Acros, DNA manipulations were performed according to standard protocols. Autoradiography was performed with a Molecular Dynamics Typhoon Phosphorimager. 1-Methyl-4-nitro-1H-imidazole-2-carboxylic acid (18a) (E. E. Baird, P. B. Dervan, *J. Am. Chem. Soc.*, 118: 6141-6146, 1996) 1-methyl-4-nitro-1H-pyrrole-2-carbaldehyde (18c) (Y. Yamamoto, T. Kimachi, Y. Kanaoka, S. Kato, K. Bessho, T. Matsumoto, T. Kusakabe. Y. Sugiura, *Tetrahedron Lett.*, 37: 7801-7804, 1996), 3-methoxy-1-methyl-4-nitro-1H-pyrrole-2-carboxylic acid ethyl ester were synthesized according to literature procedures.

The following examples are provided to further illustrate aspects of the invention. These examples are non-limiting and should not be construed as limiting any aspect of the invention.

Example 1

Synthesis of Representative Thiophene-containing Monomers

Figure 3:
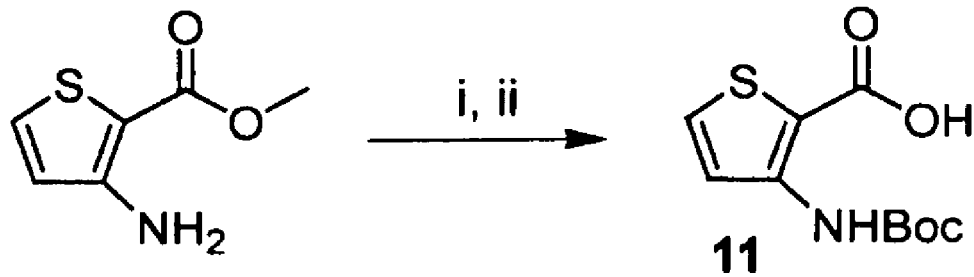
FIG. 3. (A) Synthesis of 3-[(tert-butoxy)carbonylamino]-2-thiophenecarboxylic acid (11): (i) Et$_3$N, Boc$_2$O, DMAP, acetone; (ii) 50% NaOH, MeOH. (B) Synthesis of 3-methoxy-2-thiophene-carboxylic acid (13): (iii) K$_2$CO$_3$, CH$_3$I, acetone, acetonitrile, reflux; (iv) 50% NaOH, MeOH. (C) Synthesis of 3-fluoro-2-thiophene-carboxylic acid (14): (v) nBuLi (2.2 equiv), THF, −78° C., 0.5 h; (vi) (PhSO$_2$)$_2$NF, THF, −78° C. to RT.
Figure 3:
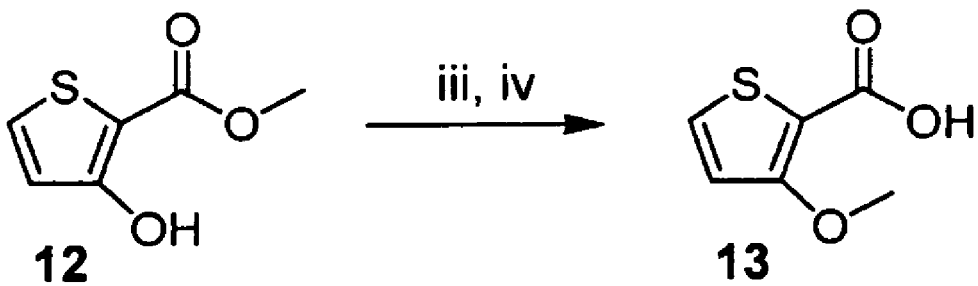
Figure 3:
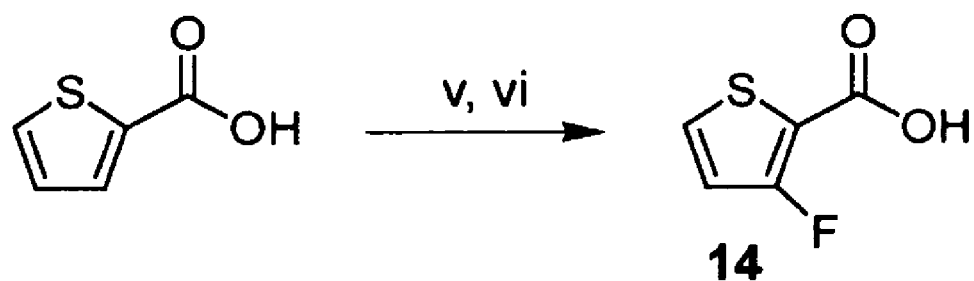
Figure 4:
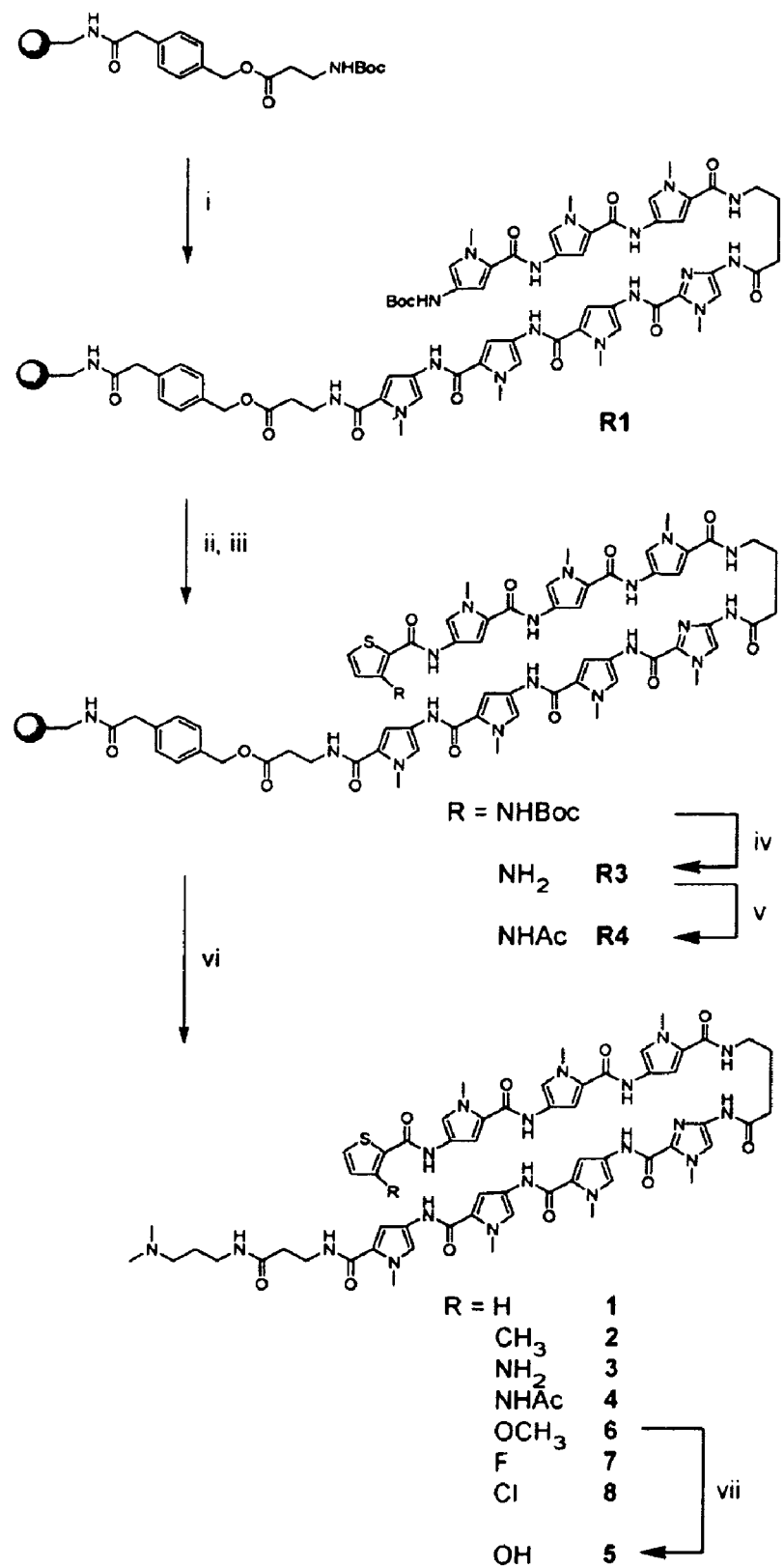
FIG. 4. Synthesis of DNA-binding polymers: (i) Synthesis of polyamide resin by standard solid-phase techniques (Baird et al., J. Am. Chem. Soc. 1996, 118, 6141) (ii) TFA, CH$_2$Cl$_2$; (iii) 3-R-thiophene-2-CO$_2$H, HBTU, DMF, DIEA; (iv) TFA, CH$_2$Cl$_2$; (v) Ac$_2$O, DMF, DIEA; (vi) Dp, 40° C.; (vii) PhSH, NaH, DMF, 100° C.
Figure 5:
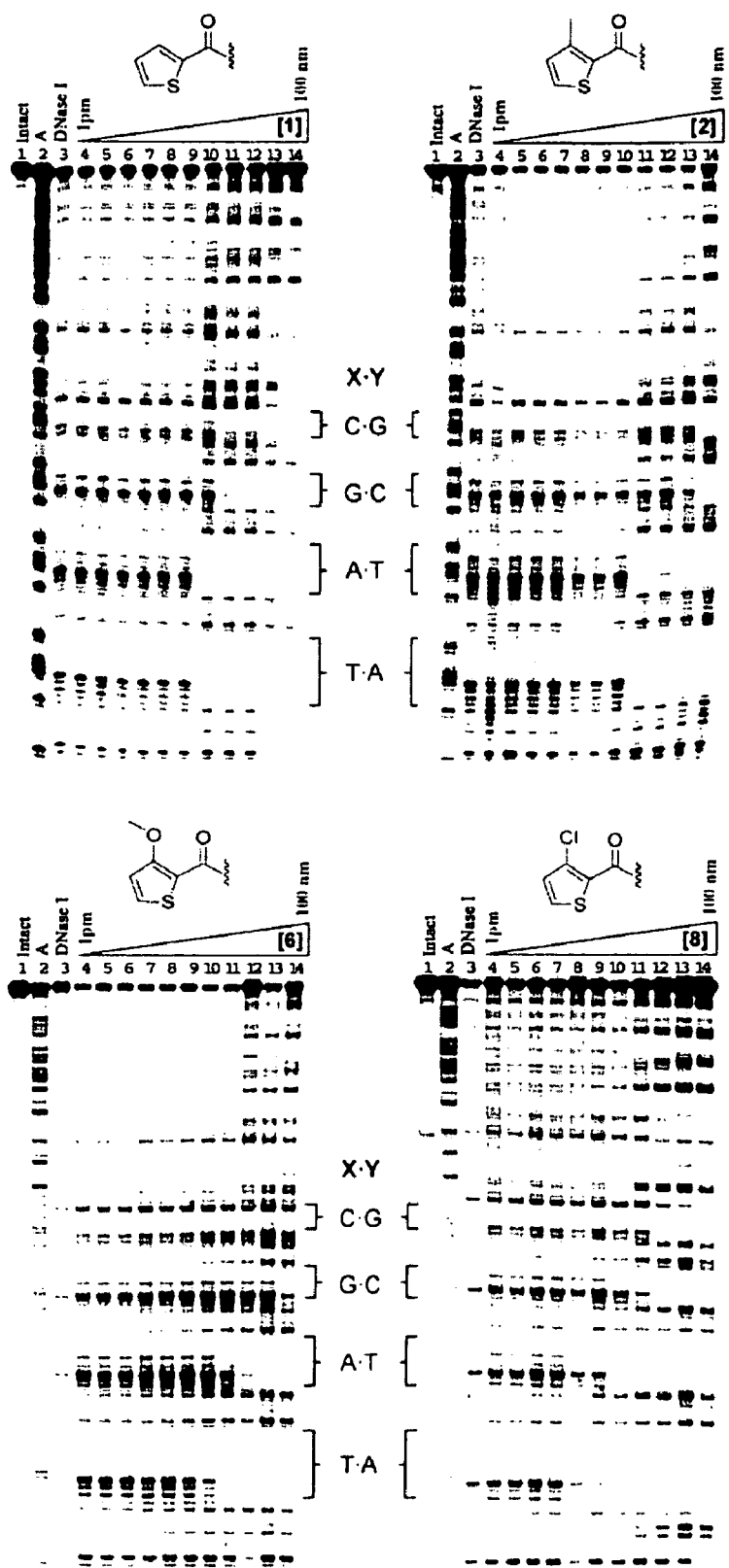
FIG. 5. Quantitative DNase I footprint titration experiments for DNA-binding polymers 1, 2, 6, and 8 on pCW15 PCR product. Lane 1, intact DNA; lane 2, A reaction; lane 3, DNase I standard; lanes 4-14, 1 pM, 3 pM, 10 pM, 30 pM, 100 pM, 300 pM, 1 nM, 3 nM, 10 nM, 30 nM, 100 nM polyamide, respectively. The chemical structure of each N-terminal residue is included at the top of the gel, and the four binding sites are labeled.

Methyl 3-aminothiophene-2-carboxylate was Boc-protected and the resulting ester was saponified to yield 3-[(tert-butoxy)carbonylamino]-2-thiophene-carboxylic acid (11). Methyl 3-hydroxythiophene-2-carboxylate (12) was prepared by cyclization of methylthioglycolate and methyl-2-chloroacrylate in methanolic sodium methoxide (Huddleston et al., Synth. Commun. 1979, 9, 731). Alkylation of (12) with iodomethane and subsequent hydrolysis of the methyl ester yielded 3-methoxy-2-thiophenecarboxylic acid (13). 3-Fluorothiophene-2-carboxylic acid (14) was synthesized as described by Taylor et al. (Org. Prep. Proc. Int. 1997, 29, 221) (FIG. 3A, 3B, 3C). The remaining 3-substituted-thiophene-2-carboxylic acids were obtained from commercial sources.

A. Preparation of 3-[(tert-Butoxy)carbonylamino]-2-thiophenecarboxylic Acid (11)

A mixture of methyl 3-amino-2-thiophene-carboxylate (2.53 g, 15.9 mmol), Boc$_2$O (7.64 g, 35 mmol), and DMAP (2.04 g, 16.7 mmol) was dissolved in acetone (15 mL) and TEA (5 mL). The reaction mixture was stirred vigorously for 4 h and diluted to a volume of 75 mL with dichloromethane. The resulting solution was washed with cold 1 N HCl (3×50 mL), 1 N NaOH (3×50 mL), and brine (50 mL). The dichloromethane solution was then dried over MgSO$_4$, filtered, and concentrated in vacuo to yield a yellow oil. The crude product was loaded onto a short plug of silica and eluted with 9:1 hexanes/ethyl acetate to yield a pale yellow solid (1.2 g) that was used without further purification. The solid was dissolved in methanol (76 mL) and 50% NaOH (4 mL) and the mixture was stirred for 4 h. The reaction was diluted to a volume of 160 mL with water and concentrated briefly in vacuo. The remaining aqueous solution was washed with diethyl ether (2×80 mL), cooled in an ice bath, and cautiously acidified to pH 2 with sulfuric acid. The suspension was washed with ethyl acetate (3×50 mL) and the combined organic washes were dried over MgSO$_4$, filtered, and concentrated in vacuo to yield (11) as a white solid (0.79 g) in 69% yield over two steps. $^1$H NMR (DMSO-d$_6$) δ 9.43 (s, 1H), 7.80 (d, J=5.4 Hz, 1H), 7.72 (d, J=5.4 Hz. 1H), 1.46 (s, 9H); $^{13}$C NMR (75 MHz, DMSO-d$_6$) δ165.8, 151.8, 144.9, 133.1, 121.2, 109.9, 81.5, 28.6; EI-MS mae 243.0563 (M+calculated 243.0565 for C$_{10}$H$_{13}$NO$_4$S).

B. Preparation of Methyl 3-hydroxy-2-thiophenecarboxylate (12)

To dry methanol (81 mL), under nitrogen, was added sodium metal (3.68 g, 304 mmol). After H$_2$ evolution ceased, the solution was cooled to 0° C. and methyl thioglycolate (10 g, 179 mmol) was added dropwise. A solution of methyl-2-chloroacrylate (10.88 g, 179 mmol) in methanol (21 mL) was then added slowly, resulting in the formation of yellow precipitate. The solution was allowed to warm to ambient temperature and stirred for 2 h. The solvent was removed in vacuo to give a dark yellow solid that was acidified to pH 2 with 4 N HCl. The resulting aqueous solution was extracted with dichloromethane (3×150 mL) and the combined organic solutions were washed with water (3×150 mL), dried over MgSO$_4$, filtered, and concentrated to give a dark oil. The oil was subjected to column chromatography on silica gel (20:1 hexanes/ethyl acetate) to give (12) (18.4 g) as a crystalline solid in 64% yield. TLC (20:1 hexanes/ethyl acetate) R$_f$ 0.47; $^1$H NMR (CDCl$_3$) δ 9.58 (s, 1H), 7.59 (d, J=5.7 Hz, 1H), 6.75 (d, J=4.8 Hz, 1H), 3.90 (s, 3H); $^{13}$C NMR (75 MHz, CDCl$_3$) δ 166.8, 164.7, 131.7, 119.4, 52.2; EI-MS m/e 158.0039 (M+ calculated 158.0038 for C$_6$H$_6$O$_3$S).

C. Preparation of 3-Methoxy-2-thiohenecarboxylic Acid (13)

A mixture of (12) (2.3 g, 14.5 mmol), K$_2$CO$_3$ (5.02 g, 36.3 mmol), and iodomethane (10.4 g, 73 mmol) was suspended in acetone (25 mL) and acetonitrile (5 mL). The resulting mixture was stirred vigorously at reflux for 3 h. The reaction was filtered and the resulting solid was washed with acetone and dichloromethane. The reaction and washes were combined and concentrated in vacuo to yield a yellow solid (1.9 g) that was used without further purification. The yellow solid was dissolved in methanol (17 mL) and 50% NaOH (3 mL) and was stirred for 3 h. The reaction was diluted to 40 mL with water and concentrated briefly in vacuo to yield a suspension. The aqueous suspension was washed with diethyl ether (2×25 mL), cooled to 0° C., and acidified to pH 2 with 10% sulfuric acid. The aqueous mixture was then washed with dichloromethane (3×50 mL) and the combined organic washes were dried over sodium sulfate, filtered, and concentrated in vacuo to give a yellow oil. The oil was suspended in 3:1 petroleum ether/dichloromethane at −20° C. overnight. Filtration gave (13) as a finely divided white solid (0.736 g) in 33% yield over two steps. TLC (4:1 ethyl acetate/hexanes) R$_f$ 0.5; $^1$H NMR (DMSO-d$_6$) δ 12.4 (s, 1H), 7.74 (d, J=5.7 Hz, 1H), 7.06 (d, J=5.4 Hz, 1H), 3.85 (s, 3H); $^{13}$C NMR (75 MHz, DMSO-d$_6$) δ 163.0, 161.9, 131.9, 118.0, 109.9, 59.4; EI-MS m/e 158.0034 (M+ calcd 158.0038 for C$_6$H$_6$O$_3$S).

D. Preparation of 3-Fluoro-2-thiophenecarboxylic Acid (14)

2-Thiophene-carboxylic acid (1.7 g, 13.3 mmol) was dissolved in anhydrous THF (30 mL) and the solution was cooled to −78° C. under Ar, with stirring. n-Butyllithium (18.3 mL, 29.3 mmol) in hexanes was added to the above solution and the mixture was stirred for 30 min. A solution of N-fluorobenzenesulfonimide (5 g, 15.9 mmol) in THF (30 mL) was then added and the resulting solution was stirred at −78° C. for 4 h and allowed to warm to ambient temperature over a period of 6 h. The reaction was diluted with diethyl ether (100 mL), cooled to 0° C., and 1 N HCl (15 mL) was added to give a biphasic mixture. The aqueous layer was isolated and washed with diethyl ether (3×50 mL). The combined ethereal layers were dried over $MgSO_4$, filtered, and concentrated in vacuo to yield an orange oil. The oil was subjected to column chromatography on silica gel using 1:1 hexanes/ethyl acetate as the eluent. (14) was obtained as a slightly brown solid (0.777 g) in 40% yield. TLC (1:1 ethyl acetate/hexanes) $R_f$ 0.17; $^1$H NMR ($CDCl_3$) δ 10.7 (s, 1H), 7.53 (dd, J=5.4, 3.6 Hz, 1H), 6.89 (d, J=5.4 Hz, 1H); $^{13}$C NMR (75 MHz, $CDCl_3$) δ 166.2 (d, J=3.5 Hz), 161.5 (d, J=278 Hz), 132.0 (d, J=10 Hz), 118.9 (d, J=24.7 Hz), 113.6; $^{19}$FNMR (282 MHz, $CDCl_3$, $CFCl_3$) δ −65.2 (d, J=6 Hz); EI-MS m/e 145.9838 (M+calcd 145.9838 for $C_5H_3FO_2S$).

Example 2

Synthesis of Representative DNA-Binding Polymers

Resin (R1) was prepared using manual solid-phase synthetic techniques described previously (Baird et al., J. Am. Chem. Soc. 1996, 118, 6141). DNA-binding polymers were synthesized from intermediate resin (R1) that was prepared according to published protocols using Boc-β-alanine-Pam resin (50 mg, 0.59 mmol/g) (e.g., Baird et al., J. Am. Chem. Soc. 1996, 118, 6141).

A. Preparation of DNA-Binding Polymer (1)

Resin (R1) was treated with 80% TFA in dichloromethane and washed thoroughly. A solution of 2-thiophenecarboxylic acid (19 mg, 0.148 mmol) and HBTU (28 mg, 0.079 mmol) in DMF (0.45 mL) and DIEA (0.5 mL) was mixed at 40° C. for 25 min and poured onto the deprotected resin. The resin slurry was shaken for 4 h at room temperature and filtered. After washing with DMF, the resin was cleaved with Dp (1 mL) at 40° C. for 4 h. The crude product was purified by reversed-phase HPLC to afford (1) as a white solid upon lyophilization (3.3 mg, 9% recovery). MALDI-TOF-MS m/z 1224.23 (1224.53 calcd for M+H).

B. Preparation of DNA-Binding Polymer (2)

Resin (R1) was treated with 80% TFA in dichloromethane and washed thoroughly. A solution of 3-methyl-2-thiophenecarboxylic acid (21 mg, 0.148 mmol) and HBTU (28 mg, 0.079 mmol) in DMF (0.45 mL) and DIEA (0.5 mL) was mixed at 40° C. for 25 min and poured onto the deprotected resin. The resin slurry was shaken for 4 h at room temperature and filtered. After washing with DMF, the resin was cleaved with Dp (1 mL) at 40° C. for 4 h. The crude product was purified by reversed-phase HPLC to afford (2) as a white solid upon lyophilization (3.0 mg, 8.2% recovery). MALDI-TOF-MS m/z 1238.35 (1238.54 calcd for M+H).

C. Preparation of DNA-Binding Polymer (3)

Resin (R1) was treated with 80% TFA in dichloromethane and washed thoroughly. Iv solution of (11) (36 mg, 0.148 mmol) and HBTU (28 mg, 0.079 mmol) in DMF (0.45 mL) and DIEA (0.5 mL) was mixed at 40° C. for 25 min and poured onto the deprotected resin. The resin slurry was shaken for 4 h at room temperature and filtered. After washing with DMF and dichloromethane, the resin was treated with 80% TFA in dichloromethane. The resin was filtered and washed before cleavage with Dp (1 mL) at 40° C. for 4 h. The crude product was purified by reversed-phase HPLC to afford (3) as a slightly yellow solid upon lyophilization (3.4 mg, 9.4% recovery). MALDI-TOF-MS m/z-1239.46 (1239.54 calcd for M+H).

D. Preparation of DNA-Binding Polymer (4)

Resin (R1) was treated with 80% TFA in dichloromethane and washed thoroughly. A solution of (11) (36 mg. 0.148 mmol) and HBTU (28 mg, 0.079 mmol) in DMF (0.45 mL) and DIFA (0.5 mL) was mixed at 40° C. for 25 min and poured onto the deprotected resin. The resin slurry was shaken for 4 h at room temperature and filtered. After washing with DMF and dichloromethane, the resin was treated with 80% TFA in dichloromethane. The resin was filtered, neutralized and shaken in a solution of acetic anhydride (0.2 mL), DIEA (0.2 mL) and DMF (1.6 mL) for 30 min. The resin was then filtered and washed with DMF before cleavage with Dp (1 mL) at 40° C. for 4 h. The crude product was purified by reversed-phase HPLC to afford (4) as a pale yellow solid upon lyophilization (4.2 mg, 11.2% recovery). MALDI-TOF-MS m/z 1281.62 (1281.55 calcd for M+H).

E. Preparation of DNA-Binding Polymer (5)

A solution of sodium hydride (40 mg, 60% oil dispersion) and thiophenol (0.1 mL) in DMF (0.15 mL) was heated to 100° C. and a solution of (6) (1.3 mg, 1 mmol) in DMF (0.25 mL) was added. After 2 h, the reaction mixture was cooled to 0° C. and 20% TFA in water (7 mL) was added. The aqueous solution was washed three times with diethyl ether (8 mL) and was subjected to preparative, reversed-phase HPLC to afford (5) as a white solid upon lyophilization (0.6 mg, 50% recovery). MALDI-TOF-MS m/z 1241.09 (1240.52 calcd for M+H).

F. Preparation of DNA-Binding Polymer (6)

Resin (R1) was treated with 80% TFA in dichloromethane and washed thoroughly. A solution of (13) (23 mg 0.148 mmol) and HBTU (28 mg, 0.079 mmol) in DMF (0.45 mL) and DIEA (0.5 mL) was mixed at 40° C. for 25 ml and poured onto the deprotected resin. The resin slurry was shaken for 4 h at room temperature and filtered. After washing with DMF and dichloromcthane, the resin was cleaved with Dp (1 mL) at 40° C. for 4 h. The crude product was purified by reversed-phase HPLC to afford (6) as a white solid upon lyophilization (3.3 mg, 8.9% recovery). MALDI-TOF-MS m/z 1255.96 (1255.39 calcd for M+H).

G. Preparation of DNA-Binding Polymer (7)

Resin (R1) was treated with 80% TFA in dichloromethane and washed thoroughly. A solution of (14) (22 mg, 0.148 mmol) and HBTU (28 mg, 0.079 mmol) in DMF (0.45 mL) and DIEA (0.5 mL) was mixed at 40° C. for 25 ml and poured onto the deprotected resin. The resin slurry was shaken for 4 h at room temperature and filtered. After washing with DMF and dichloromethane, the resin was cleaved with Dp (1 mL) at 40° C. for 4 h. The crude product was purified by reversed-phase HPLC to afford (7) as a white solid upon lyophilization (2.6 mg, 7.0% recovery). MALDI-TOF-MS m/z 1242.20 (1242.52 calcd for M+H).

H. Preparation of DNA-Binding Polymer (8)

Resin (R1) was treated with 80% TFA in dichloromethane and washed thoroughly. A solution of 3-chloro-2-thiophenecarboxylic acid (24 mg, 0.148 mmol) and HBTU (28 mg, 0.079 mmol) in DMF (0.45 mL) and DIEA (0.5 mL) was mixed at 40° C. for 25 min and poured onto the deprotected resin. The resin slurry was shaken for 4 h at room temperature and filtered. After washing with DMF and dichloromethane, the resin was cleaved with Dp (1 mL) at 40° C. for 4 h. The crude product was purified by reversed-phase HPLC to afford (8) as a white solid upon lyophilization (3.8 mg, 10.1% recovery). MALDI-TOF-MS m/z 1258.86 (1258.49 calcd for M+H).

I. Preparation of DNA-Binding Polymer (9)

DNA-binding polymer (9), which contains an N-terminal N-methylimidazole (Im) was used as a control polymer. Resin (R1) was treated with 80% TFA in dichloromethane and washed thoroughly. A solution of 2-trichloroacetyl-1-methylimidazole (34 mg, 0.148 mmol) in DMF (0.45 mL) and DIEA (0.5 mL) was poured onto the deprotected resin. The resin slurry was shaken for 4 h at 40° C. and filtered. After washing with DMF and dichloromethane, the resin was cleaved with Dp (1 mL) at 40° C. for 4 h. The crude product was purified by reversed-phase HPLC to afford (9) as a yellow solid upon lyophilization (2.5 mg, 6.9% recovery). MALDI-TOF-MS m/z 1222.03 (1222.58 calcd for M+H).

J. Preparation of DNA-Binding Polymer (10)

DNA-binding polymer (10), which contains an N-terminal N-methylpyrrole (Py), was used as a control polymer. Resin (R1) was treated with 80% TFA in dichloromethane and washed thoroughly. A solution of N-methylpyrrole-2-carboxylic acid (19 mg, 0.148 mmol) and HBTU (28 mg, 0.079 mmol) in DMF (0.45 mL) and DIEA (0.5 mL) was mixed at 40° C. for 25 min and poured onto the deprotected resin. The resin slurry was shaken for 4 h at room temperature and filtered. After washing with DMF and dichloromethane, the resin was cleaved with Dp (1 mL) at 40° C. for 4 h. The crude product was purified by reversed-phase HPLC to afford (10) as a white solid upon lyophilization (2.7 mg, 7.5% recovery). MALDI-TOF-MS m/z 1222.12 (1221.58 calcd for M+H).

Example 3

DNA Binding Energetics of Representative DNA-Binding Polymers

A. DNA Reagents and Materials for DNase Footprinting

Oligonucleotide primers SF1 (5'-AATTC-GAGCTCGG-TACCGGGG-3'; SEQ ID NO:1) and SF2(5'-CTGGCACGA-CAGGTTTCCCGA-3'; SEQ ID NO:2) were synthesized by the Biopolymer Synthesis Center at the California Institute of Technology. Products from PCR amplification of the pCW15 using 5'-[γ-$^{32}$P]-labeled SF1 and SF2 were purified on a 7% non-denaturing polyacrylamide gel. Glycogen (20 mg/mL), dNTPs (PCR nucleotide mix), and all enzymes, unless otherwise stated, were purchased from Boehringer-Mannheim. Deoxyadenosine [γ-$^{32}$P]triphosphate was obtained from ICN. Calf thymus DNA (sonicated, deproteinized) and DNase I (7500 units/mL. FPLC pure) were from Amersham Pharmacia. AmpliTaq DNA polymerase was obtained from Perkin-Elmer and was used with provided buffers. Tris.HCl, DTT, RNase-free water, and 0.5 M EDTA were from United States Biochemical. Calcium chloride, potassium chloride, and magnesium chloride were purchased from Fluka. Tris-borate-EDTA was from GIBCO and bromophenol blue was from Acros. All reagents were used without further purification.

B. DNase I Footprinting Experiments

The DNA sequence specificity of novel thiophene-2-carboxamide-containing polymers (DNA-binding polymers 1-8) was evaluated by comparing their affinities for each Watson-Crick base pair to those of N-methylimidazole (Im) and N-methylpyrrole (Py) (DNA-binding polymers 9-10). Table 3 shows the effect of substitution on the N-terminal thiophene of each of the thiophene-containing DNA-binding polymers (DNA-binding polymers 1-8). Affinities were determined using DNase I footprinting, as performed by standard protocols (e.g., Trauger et al., Methods Enzymol. 2001, 340, 450).

TABLE 3

Equilibrium association constants $(M^{-1})^a$.

| DNA-binding polymer | Ring Pairing | R | T-A | A-T | G-C | C-G |
|---|---|---|---|---|---|---|
| 1 | Tp(1)Py | H | 6.0 (0.7) × 10$^9$ | 4.7 (0.7) × 10$^9$ | 4.3 (0.4) × 10$^8$ | 2.2 (0.3) × 10$^9$ |
| 2 | Tp(2)Py | CH$_3$ | 2.3 (0.4) × 10$^9$ | 1.4 (0.2) × 10$^9$ | 1.0 (0.4) × 10$^7$ | 1.0 (0.3) × 10$^7$ |
| 3 | Tp(3)Py | NH$_2$ | 6.3 (1.0) × 10$^9$ | 4.6 (0.6) × 10$^9$ | 7.8 (0.9) × 10$^8$ | 2.2 (0.3) × 10$^8$ |
| 4 | Tp(4)Py | NHA$_C$ | 5.9 (0.3) × 10$^9$ | 2.9 (0.1) × 10$^9$ | 6.6 (0.4) × 10$^8$ | 6.0 (0.2) × 10$^8$ |
| 5 | Tp(5)Py | OH | 6.2 (0.6) × 10$^9$ | 4.5 (0.6) × 10$^9$ | 2.1 (0.3) × 10$^8$ | 8.4 (0.1) × 10$^7$ |
| 6 | Tp(6)Py | OCH$_3$ | 2.0 (0.4) × 10$^9$ | 3.2 (0.6) × 10$^8$ | ≦1.0 × 10$^7$ | ≦1.0 × 10$^7$ |
| 7 | Tp(7)Py | F | 1.2 (0.2) × 10$^{10}$ | 3.9 (0.3) × 10$^9$ | 3.7 (0.4) × 10$^8$ | 2.9 (0.3) × 10$^8$ |
| 8 | Tp(8)Py | Cl | 1.3 (0.2) × 10$^{10}$ | 3.7 (0.2) × 10$^9$ | 3.1 (0.6) × 10$^8$ | 2.1 (1.1)× 10$^8$ |
| 9 | Im/Py | | 3.8 (0.3) × 10$^9$ | 2.8 (0.2) × 10$^9$ | 7.0 (0.9) × 10$^{10}$ | 3.2 (0.4) × 10$^9$ |
| 10 | Py/Py | | 5.1 (0.6) × 10$^9$ | 3.1 (0.3) × 10$^9$ | 1.1 (0.1) × 10$^9$ | 2.6 (0.3) × 10$^8$ |

$^a$Values reported are mean results determined by at least three DNase I footprint titrations, with standard deviation given in parentheses. Assays were performed at 22° C. in a buffer containing 10 mM Tris-HCl, 10 mM KCl, 10 mM MgCl2, and 5 mM CaCl2 at pH 7.0

Briefly, Quantitative DNase I footprinting titration experiments (10 mM Tris-HCl. 10 mM KCl, 10 mM MgC$_2$, 5 mM CaCl$_2$, pH 7.0, 22° C.) were performed on 5'-$^{32}$P end-labeled, 285 bp PCR product from plasmid construct pCW15 (as described previously in Ellervik et al., J. Am. Chem. Soc. 2000, 122, 9354). This plasmid contains four binding sites that vary at a single N-terminal position, 5'-A T N T A C A-3', where N=T, A, G, C. The equilibrium association constant for each N-terminal ring pairing with each Watson-Crick base pair is shown in Table 3. The divergent behavior of control DNA-binding polymers 9 and 10 illustrates the need for development of new N-terminal residues. A terminal Im/Py pairing of DNA-binding polymer 9 binds its match sequence, 5'-A T G T A C A-3', with high affinity ($K_a$=7×10 M$^{-1}$) while showing >15-fold preference for G-C relative to T-A, A-T, and C-G base pairs. Terminal Py/Py pairings of DNA-binding polymer 10, on the other hand, are characterized by little sequence specificity, binding T-A, A-T, and G-C with comparable affinity (Table 3).

Figure 6:
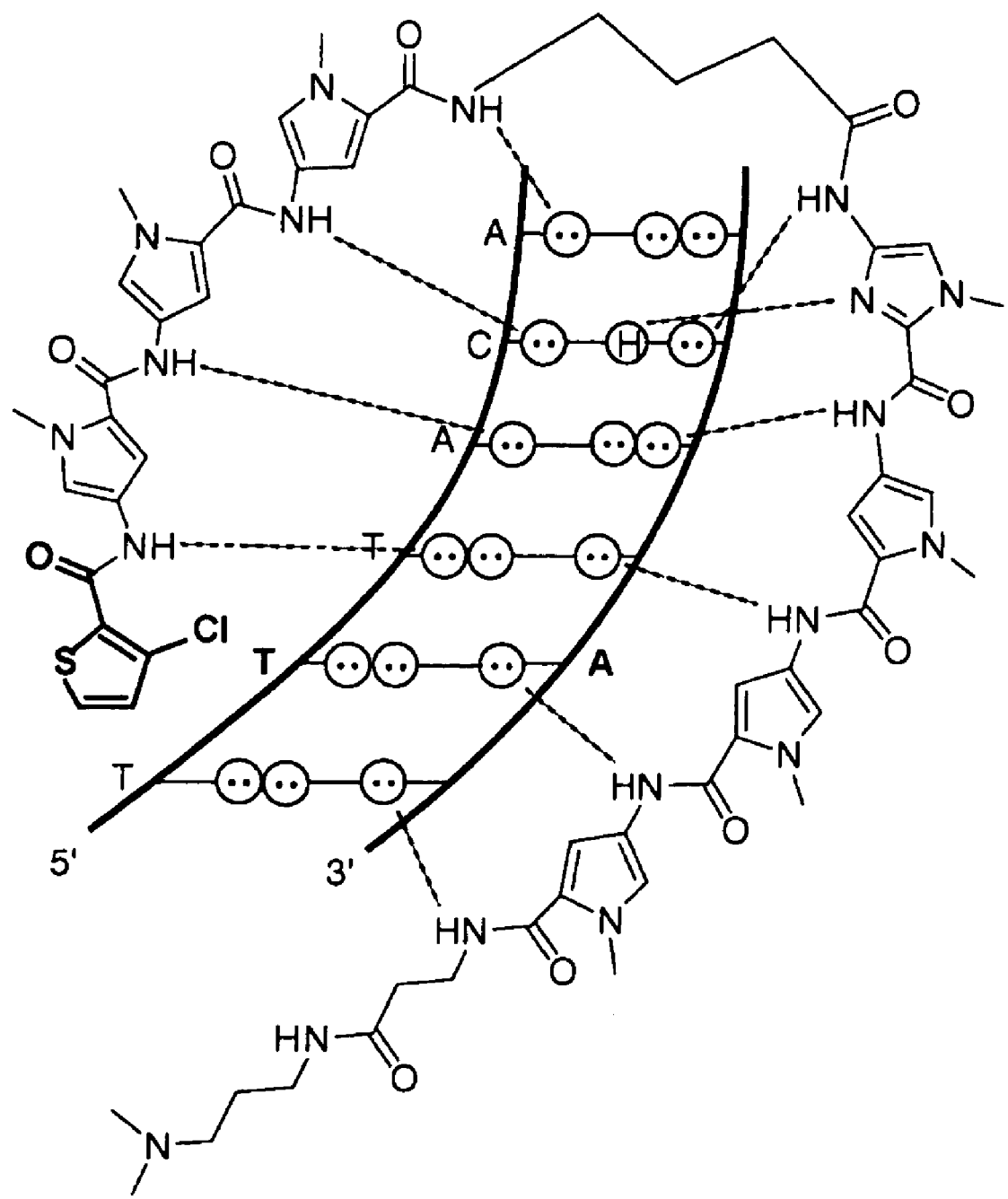
FIG. 6. Hypothetical binding model to explain selectivity for T-A over A-T. The thiophene is in the anti conformation (sulfur away from the groove) and the 3-chloro substituent points to the minor groove floor.

Within the thiophene-2-carboxamide series, an unsubstituted thiophene ring paired with Py (i.e., DNA-binding polymer 1) shows little sequence specificity. Addition of a methyl group at the 3-position (i.e., DNA-binding polymer 2) exerts a dramatic effect on sequence specificity: A-T favored over G-C. DNA-binding polymer 2 binds both T-A and A-T with a 140-fold preference for T-A relative to G-C. Amino, acetamido, or hydroxyl substituents at the 3-position of thiophene (i.e., DNA-binding polymer s 3, 4, and 5, respectively) all distinguish T-A from G-C but again do not distinguish T-A from A-T. Remarkably, a 3-methoxythiophene paired with Py (i.e., DNA-binding polymer 6) shows good affinity for T-A ($K_a=2\times10^9$ $M^{-1}$) with 6-fold selectivity for T-A relative to A-T and >200-fold specificity relative to G-C. Fluoro and chloro substituted thiophene, (i.e., DNA-binding polymers 7 and 8, respectively), paired with Py afford higher binding affinities for T-A but a lower selectivity (3-fold) for T-A over A-T (see FIG. 6).

Example 4

Molecular Modeling

Molecular modeling was performed using the *Spartan Essential* software package (Wavefunction Inc.). N-Terminal residues were first minimized as methyl-2-carboxamides using an AM1 model. The resulting geometry was then subjected to ab initio calculation using the Hartree-Fock model with a 6-31G* polarization basis set. The partial electrostatic charge of the sulfur atom, $\delta_S$, and the partial charge of the peripheral atom of the 3-substituent. $\delta_R$, were examined for each thiophene residue. The electronic influences of 3-substituents on the polarization of the sulfur atom follow expected trends, with partial electronic charge, $\delta_S$, decreasing as follows: 4>7>1>6>5>8>2>3. The electronic surfaces presented by the 3-substituents, $\delta_R$ were also calculated and found to decrease as follows: 5>3>4>1>6>2>7>8 (Table 4).

TABLE 4

Physical properties determined by molecular modeling[a]

| Polyamide | R | $d_S^b$ | $dR^b$ (R)[c] | $E_{syn} - E_{anti}^d$ | $A_R/A_H^e$ |
|---|---|---|---|---|---|
| 1 | H | −0.065 | 0.124, (CH) | 0.262 | 1.00 |
| 2 | CH₃ | −0.093 | 0.036, (CH₃) | 1.739 | 1.11 |
| 3 | NH₂ | −0.117 | 0.426, (NH₂) | 10.289 | 1.07 |
| 4 | NHA_C | −0.057 | 0.320, (NH) | 10.308 | 1.31 |
| 5 | OH | −0.069 | 0.512, (OH) | 7.142 | 1.04 |
| 6 | OCH₃ | −0.068 | 0.063, (OCH₃) | −7.298 | 1.17 |
| 7 | F | −0.061 | −0.227, (F) | −5.043 | 1.03 |
| 8 | Cl | −0.076 | −0.106, (Cl) | −13.293 | 1.09 |

[a]Ab initio calculations were performed with Spartan Essential software package using Hartree-Fock model with 6-31G* polarization basis set.
[b]Partial electrostatic charges are given in arbitrary units.
[c]Partial charges given for atoms in bold.
[d]Energy differences are reported in kcal/mol.
[e]Ratio of surface area, A, of 3-substituent to hydrogen.

The relative energy differences between minimized syn and anti conformations was also examined for each thiophene ring. DNA-binding polymers 1-5 show a preference for the anti, or "sulfur down," conformation, which may be attributed to lone pair repulsions between the sulfur atom and the carbonyl oxygen of the 2-carboxamide moiety. This bias can be reinforced by favorable hydrogen bonding interactions between 3-substituents and the carboxamide as in DNA-binding polymers 3-5. By contrast, DNA-binding polymers 68 display a bias for the syn, or "sulfur up," conformation, possibly owing to more severe electronic clashes between the electron rich 3-substituents and the carboxamide relative to those of the sulfur atom. Finally, the solvent exposed surface area of each 3-substituted thiophene was compared to the unsubstituted thiophene ring to assess the steric contribution of the 3-substituent and surface area was found to increase in the following order: 1<7<5<3<8<2<6<4.

The observed equilibrium association constants for DNA-binding polymers 1-5 support an anti conformation for the N-terminal thiophene residue. The binding preference of these compounds for T-A/A-T relative to G-C/C-G might be a result of unfavorable steric clashes between the sulfur atom and the exocyclic amino group of guanine. The binding properties of N-terminal, 3-methylthiophene-2-carboxamide residues also correlate well with values derived from internal contexts, where the sulfur down conformation is stringently enforced (Marques et al, Helv. Chim. Acta 2002, 85, 4485).

N-Terminal 3-methoxy (or 3-chloro) thiophene-2-carboxamide residues when paired with Py demonstrate selectivity for T-A versus A-T. This discovery allows one to expand the array of DNA sequences that can be targeted by minor groove-binding polyamides.

While the invention has been described in detail with reference to certain preferred embodiments thereof, it will be understood that modifications and variations are within the spirit and scope of that which is described and claimed.

That which is claimed is:

1. A method for modulating the expression of a gene, said method comprising:

contacting said gene with an effective amount of a DNA-binding polymer under conditions such that said DNA-binding polymer binds to a double stranded portion of said gene, thereby modulating the expression of said gene, wherein said DNA binding polymer comprises:

a first terminus, an oligomeric backbone optionally containing a linking element, and a second terminus;

wherein:

said first terminus is an optionally substituted thiophene-containing moiety;

said oligomeric backbone comprises a plurality of optionally substituted monomer elements;

said second terminus is selected from the group consisting of optionally substituted N-methylpyrrole, optionally substituted N-methylimidazole, and optionally substituted benzimidazole moiety;

said DNA-binding polymer is effective to bind to a double-stranded DNA sequence having a number of DNA base pairs in the range (n/2) to (2n) where n is the number of monomer elements in said DNA-binding polymer; and said first terminus and said second terminus of said DNA-binding polymer are effective in combination to bind to a T-A DNA base pair.

2. A method according to claim 1 wherein said double-stranded portion of said gene is a regulatory sequence.

3. A method according to claim 1 wherein said double-stranded portion of said gene is a promoter sequence.

4. A method according to claim 1 wherein said double-stranded portion of said gene is a coding sequence.

5. A method according to claim 1 wherein said double-stranded portion of said gene is a non-coding sequence.

6. A method according to claim 1 wherein said optionally substituted thiophene-containing moiety is optionally substituted with a substituent selected from the group consisting of $C_{1-6}$ alkyl, substituted $C_{1-6}$ alkyl, —$NR_1R_2$, —NHC(=O)$R_3$, halo, hydroxy, alkoxy, aryloxy, heteroaryloxy, arylalkoxy, and heteroarylalkoxy;
wherein:
$R_1$ and $R_2$ at each occurrence are independently selected from the group consisting of hydrogen, $C_{1-6}$ alkyl, substituted $C_{1-6}$ alkyl, aryl, substituted aryl, heteroaryl, substituted heteroaryl, arylalkyl, substituted arylalkyl, heteroarylalkyl, and substituted heteroarylalkyl; and
$R_3$ is $C_{1-6}$ alkyl.

7. A method according to claim 1 wherein said optionally substituted thiophene-containing moiety is selected from the group consisting of thiophene, benzthiophene, C—C linked benzimidazole/thiophene-containing moiety and C—C linked hydroxybenzimidazole/thiophene-containing moiety.

8. A method according to claim 1 wherein the second terminus is substituted with substituted β-alanine.

9. A method according to claim 1 wherein said second terminus is further substituted with a biochemically reactive substituent or detectable substituent.

10. A method according to claim 9 wherein said biochemically reactive substituent is selected from the group consisting of —NH(CH$_2$)$_{0-100}$NR$_4$R$_5$, —NH(CH$_2$)$_{0-12}$CONH(CH$_2$)$_{0-100}$NR$_4$R$_5$, and —NHR$_4$;
wherein:
$R_4$ and $R_5$ are independently selected from the group consisting of: H, Cl, NO, N-acetyl, benzyl, $C_{1-100}$ alkyl, $C_{1-100}$ alkylamine, $C_{1-100}$ alkyldiamine, $C_{1-100}$ alkylcarboxylate, $C_{2-100}$ alkenyl, $C_{2-100}$ alkynyl, and $C_{1-100}$ alkyl-Z, wherein Z is selected from the group consisting of arylboronic acids, biotins, polyhistidines comprised from about 2 to 8 amino acids, haptens, solid phase supports, oligodeoxynucleotides, N-ethylnitrosourea, bromoacetamide, iodoacetamide, camptothecin, and mitomycin.

11. A method according to claim 9 wherein said detectable substituent is selected from the group consisting of: a fluorescein, Oregon Green, BODIPY, verapamil, DL-α-lipoic acid, an acridine, a pyrene, texas red, an anthracene, an anthracene derivative, anthrinilic acid, avidin, DAPI, isosulfan blue, malachite green, psoralen, ethyl red, 4-(psoraen-8-yloxy)-butyrate, tartaric acid, and (+)-α-tocopheral.

12. A method according to claim 1 wherein said oligomeric backbone comprises a plurality of optionally substituted monomer elements wherein:
each monomer element is independently selected from the group consisting of optionally substituted bifunctional heterocycle and β-alanine, and
the monomer elements are linked by carboxamide bonds or by direct ring carbon-ring carbon (C—C) bonds.

13. A method according to claim 12 wherein said oligomeric backbone has the formula:

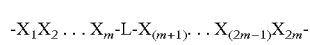

wherein:
each $X_1$, $X_2$, $X_m$, $X_{(m+1)}$, $X_{(2m-1)}$, and $X_{2m}$ is independently a monomer element in the binding pairs $X_1/X_{2m}$, $X_2/X_{(2m-1)}$, ..., $X_m/X_{(m+1)}$;

L is an optional linking element, and
m falls in the range of 1 up to 10.

14. A method according to claim 13, wherein said oligomeric backbone comprises a plurality of monomer elements, wherein:
each monomer element is independently selected from the group consisting of optionally substituted pyrrole carboxamide monomer, optionally substituted imidazole carboxamide monomer, optionally substituted C—C linked heteromonocyclic/heterobicyclic moiety, and β-alanine;
wherein:
said optionally substituted pyrrole carboxamide monomers have the structure:

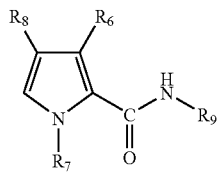

wherein:
$R_6$ is selected from the group consisting of H, $CH_3$, $C_1$, $CF_3$, OH and $NH_2$;
$R_7$ is selected from the group consisting of H, $C_{1-10}$ alkyl, $C_{2-10}$ alkenyl, and $C_{2-10}$ alkynyl;
$R_8$ is selected from the group consisting of hydrogen and a covalent bond; and
$R_9$ is a covalent bond;
wherein:
said optionally substituted imidazole carboxamide monomers have the structure:

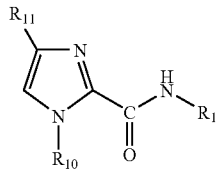

wherein:
$R_{10}$ is selected from the group consisting of $C_{1-10}$ alkyl, $C_{2-10}$ alkenyl, and $C_{2-10}$ alkynyl;
$R_{11}$ is selected from the group consisting of hydrogen and a covalent bond; and
$R_{12}$ is a covalent bond;
wherein:
said optionally substituted C—C linked heteromonocyclic/heterobicyclic moiety has the structure:

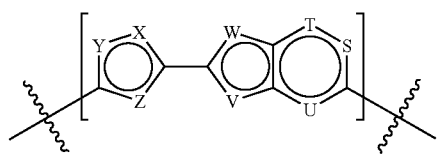

wherein:
each of S, T, and U is independently —$CR_{13}$ or N;
each of V, W, X, Y and Z is independently —$CR_{14}$, N, —$NR_{15}$, O, or S; and each $R_{13}$ is independently H, halogen, —OH, —OMe, —OAc, —NH$_2$, —NHAc, —CH$_3$, —SH, —NO$_2$, —CHO, —SO$_2$H, —S(O)NH$_2$, —(C=C)(CN)$_3$, —CN, acetyl, $C_{1-6}$ alkyl, or $C_{1-6}$ alkylamino; and each of $R_{14}$ and $R_{15}$ is independently H, halogen, —OH, —OMe, —SH, —CN, —OAc, —NH$_2$, —NHAc, $C_{1-6}$ alkyl, $C_{1-6}$ alkylamino, $C_{2-6}$ alkenyl or $C_{2-6}$ alkynyl;

or a pharmaceutically acceptable salt thereof.

15. A method of claim 13, wherein said binding pairs are selected from the group consisting of Im/Py, Py/Im, Py/Py, Hp/Py, Py/Hp, Tn Py, Py/Tn, Ht/Py, Py/Ht, Bi/Py, Py/Bi, Bi/Im, Im/Bi, Hz/Py, Py/Hz, Ip/Py Py/Ip, Bi/Hz, Hz/Bi, Bi/Bi Th/Py, Py/Th, and any of the above wherein Hp and Py monomers of said carboxamide binding pairs are replaced with β-alanine.

16. A method according to claim 13, wherein said linking element is selected from the group consisting of optionally substituted alkylene, optionally substituted alkenylene, and optionally substituted polyethylene glycol diyl.

17. A method according to claim 13, wherein said linking element is selected from the group consisting of γ-aminobutyric acid and 2,4-diaminobutyric acid.

18. A method of claim 13, wherein at least three consecutive monomer element pairs bind to at least three DNA base pairs.

19. A method for inhibiting transcription of a gene in an organism, said method comprising:
    administering to said organism an effective amount of one or more DNA-binding oligomers, selected so as to provide specific binding either singly or in pairs to a target double stranded DNA in a minor groove target site of said double stranded DNA, wherein said DNA-binding polymer comprises:
    a first terminus,
    an oligomeric backbone optionally containing a linking element, and
    a second terminus;
    wherein:
        said first terminus is an optionally substituted thiophene-containing moiety;
        said oligomeric backbone comprises a plurality of optionally substituted monomer elements;
        said second terminus is selected from the group consisting of optionally substituted N-methylpyrrole, optionally substituted N-methylimidazole, and optionally substituted benzimidazole moiety;
        said DNA-binding polymer is effective to bind to a double-stranded DNA sequence having a number of DNA base pairs in the range (n/2) to (2n) where n is the number of monomer elements in said DNA-binding polymer; and
        said first terminus and said second terminus of said DNA-binding polymer are effective in combination to bind to a T-A DNA base pair.

20. The method of claim 19, wherein said organism is a mammal.

21. A method of binding a polymer to double stranded DNA, said method comprising:
    contacting said double stranded DNA with an effective amount of a DNA-binding polymer under conditions such that said DNA-binding polymer binds to said double stranded DNA, wherein said DNA binding polymer comprises:
    a first terminus,
    an oligomeric backbone optionally containing a linking element, and
    a second terminus;
    wherein:
        said first terminus is an optionally substituted thiophene-containing moiety;
        said oligomeric backbone comprises a plurality of optionally substituted monomer elements;
        said second terminus is selected from the group consisting of optionally substituted N-methylpyrrole, optionally substituted N-methylimidazole, and optionally substituted benzimidazole moiety;
        said DNA-binding polymer is effective to bind to a double-stranded DNA sequence having a number of DNA base pairs in the range (n/2) to (2n) where n is the number of monomer elements in said DNA-binding polymer; and
        said first terminus and said second terminus of said DNA-binding polymer are effective in combination to bind to a T-A DNA base pair.

* * * * *